United States Patent
Jacobson et al.

(10) Patent No.: US 11,015,191 B2
(45) Date of Patent: May 25, 2021

(54) METHODS AND DEVICES FOR HIGH FIDELITY POLYNUCLEOTIDE SYNTHESIS

(71) Applicant: Gen9, Inc., Cambridge, MA (US)

(72) Inventors: Joseph Jacobson, Newton, MA (US); George Church, Brookline, MA (US); Larry Li-Yang Chu, Cambridge, MA (US)

(73) Assignee: Gen9, Inc., Boston, MA (US)

( * ) Notice: Subject to any disclaimer, the term of this patent is extended or adjusted under 35 U.S.C. 154(b) by 562 days.

(21) Appl. No.: 15/814,826

(22) Filed: Nov. 16, 2017

(65) Prior Publication Data

US 2018/0163200 A1  Jun. 14, 2018

Related U.S. Application Data

(62) Division of application No. 14/317,082, filed on Jun. 27, 2014, now Pat. No. 9,856,471, which is a division of application No. 13/060,178, filed as application No. PCT/US2009/055267 on Aug. 27, 2009, now Pat. No. 8,808,986.

(60) Provisional application No. 61/235,677, filed on Aug. 20, 2009, provisional application No. 61/092,309, filed on Aug. 27, 2008.

(51) Int. Cl.
| | |
|---|---|
| C12Q 1/68 | (2018.01) |
| C12Q 1/6837 | (2018.01) |
| C07H 21/00 | (2006.01) |
| C12N 15/10 | (2006.01) |
| B01L 3/02 | (2006.01) |
| B01L 3/00 | (2006.01) |
| C12Q 1/6844 | (2018.01) |
| C12N 15/66 | (2006.01) |

(52) U.S. Cl.
CPC ........ *C12N 15/1093* (2013.01); *B01L 3/0268* (2013.01); *B01L 3/502792* (2013.01); *C12N 15/10* (2013.01); *C12N 15/66* (2013.01); *C12Q 1/6837* (2013.01); *C12Q 1/6844* (2013.01); *B01J 2219/0052* (2013.01); *B01J 2219/0059* (2013.01); *B01J 2219/00378* (2013.01); *B01J 2219/00389* (2013.01); *B01J 2219/00529* (2013.01); *B01J 2219/00585* (2013.01); *B01J 2219/00596* (2013.01); *B01J 2219/00599* (2013.01); *B01J 2219/00608* (2013.01); *B01J 2219/00659* (2013.01); *B01J 2219/00693* (2013.01); *B01J 2219/00722* (2013.01); *B01L 2400/0436* (2013.01); *B01L 2400/0439* (2013.01)

(58) Field of Classification Search
CPC ...... C12Q 1/68; C12Q 1/6837; C12Q 1/6874; C07H 21/00; C12N 15/10; C12N 15/1093; B01J 2219/00529
See application file for complete search history.

(56) References Cited

U.S. PATENT DOCUMENTS

| | | |
|---|---|---|
| 5,143,854 A | 9/1992 | Pirrung et al. |
| 5,288,514 A | 2/1994 | Ellman |
| 5,384,261 A | 1/1995 | Winkler et al. |
| 5,510,270 A | 4/1996 | Fodor et al. |
| 5,514,789 A | 5/1996 | Kempe |
| 5,527,681 A | 6/1996 | Holmes |
| 5,541,061 A | 7/1996 | Fodor et al. |
| 5,639,603 A | 6/1997 | Dower et al. |
| 5,700,637 A | 12/1997 | Southern |
| 5,700,642 A | 12/1997 | Monforte et al. |
| 5,738,829 A | 4/1998 | Kempe |
| 5,739,386 A | 4/1998 | Holmes |
| 5,770,358 A | 6/1998 | Dower et al. |
| 5,830,655 A | 11/1998 | Monforte et al. |
| 5,989,402 A | 11/1999 | Chow et al. |
| 6,042,211 A | 3/2000 | Hudson et al. |
| 6,248,521 B1 | 6/2001 | Van Ness et al. |
| 6,375,903 B1 | 4/2002 | Cerrina et al. |
| 6,416,164 B1 | 7/2002 | Stearns et al. |
| 6,511,849 B1 | 1/2003 | Wang |

(Continued)

FOREIGN PATENT DOCUMENTS

| | | |
|---|---|---|
| EP | 1205548 A1 | 5/2002 |
| WO | WO-9000626 A1 | 1/1990 |

(Continued)

OTHER PUBLICATIONS

Parsons, BL. Evaluation of MutS as a tool for direct measurement of point mutations in genomic DNA. Mutation Research 374(2) : 277-285 (Year: 1997).*

Sun et al., MutS-Mediated Detection of DNA Mismatches using Atomic Force Microscopy. Analytical Chemistry 72 :3138-3141 (Year: 2000).*

Adessi, C., et al. "Solid phase DNA amplification: characterization of primer attachment and amplification mechanisms," Nucleic Acids Research, 28(20):e87, (2000).

Ashkin, A., "Applications of laser radiation pressure" Science, 210(4474): 1081-1088, (Dec. 5, 1980).

(Continued)

*Primary Examiner* — Ethan C Whisenant

(74) *Attorney, Agent, or Firm* — Wolf, Greenfield & Sacks, P.C.

(57) ABSTRACT

Disclosed are methods for synthesizing and/or assembling at least one polynucleotide product having a predefined sequence from a plurality of different oligonucleotides. In exemplary embodiments, the methods involve synthesis and/or amplification of different oligonucleotides immobilized on a solid support, release of synthesized/amplified oligonucleotides in solution to form droplets, recognition and removal of error-containing oligonucleotides, moving or combining two droplets to allow hybridization and/or ligation between two different oligonucleotides, and further chain extension reaction following hybridization and/or ligation to hierarchically generate desired length of polynucleotide products.

16 Claims, 12 Drawing Sheets

(56) References Cited

U.S. PATENT DOCUMENTS

| | | | |
|---|---|---|---|
| 6,514,704 | B2 | 2/2003 | Bruce et al. |
| 6,596,239 | B2 | 7/2003 | Williams et al. |
| 6,658,802 | B2 | 12/2003 | Lucas, Jr. et al. |
| 6,664,388 | B2 | 12/2003 | Nelson |
| 6,800,439 | B1 | 10/2004 | McGall et al. |
| 6,802,593 | B2 | 10/2004 | Ellson et al. |
| 6,824,866 | B1 | 11/2004 | Glazer et al. |
| 6,830,890 | B2 | 12/2004 | Lockhart et al. |
| 6,833,450 | B1 | 12/2004 | McGall et al. |
| 6,911,132 | B2 | 6/2005 | Pamula et al. |
| 6,932,097 | B2 | 8/2005 | Ellson et al. |
| 7,090,333 | B2 | 8/2006 | Mutz et al. |
| 7,133,782 | B2 | 11/2006 | Odedra |
| 7,169,560 | B2 | 1/2007 | Lapidus et al. |
| 7,323,320 | B2 | 1/2008 | Oleinikov |
| 7,563,600 | B2 | 7/2009 | Oleinikov |
| 8,338,091 | B2 | 12/2012 | Chesnut et al. |
| 8,808,986 | B2* | 8/2014 | Jacobson .......... B01L 3/502792 435/6.1 |
| 9,856,471 | B2* | 1/2018 | Jacobson .......... C12N 15/1093 |
| 2001/0012537 | A1 | 8/2001 | Anderson et al. |
| 2001/0053519 | A1 | 12/2001 | Fodor et al. |
| 2002/0037579 | A1 | 3/2002 | Ellson et al. |
| 2002/0081582 | A1 | 6/2002 | Gao et al. |
| 2003/0047688 | A1 | 3/2003 | Faris et al. |
| 2003/0068633 | A1 | 4/2003 | Belshaw et al. |
| 2003/0171325 | A1 | 9/2003 | Gascoyne et al. |
| 2003/0186226 | A1 | 10/2003 | Brennan et al. |
| 2003/0215837 | A1 | 11/2003 | Frey et al. |
| 2004/0009479 | A1 | 1/2004 | Wohlgemuth et al. |
| 2004/0101894 | A1 | 5/2004 | Albert et al. |
| 2004/0106728 | A1 | 6/2004 | McGall et al. |
| 2004/0152094 | A1 | 8/2004 | Danielsen et al. |
| 2004/0161741 | A1 | 8/2004 | Rabani et al. |
| 2004/0185484 | A1 | 9/2004 | Costa et al. |
| 2005/0019776 | A1 | 1/2005 | Callow et al. |
| 2005/0079510 | A1 | 4/2005 | Berka et al. |
| 2005/0202429 | A1 | 9/2005 | Trau et al. |
| 2005/0227235 | A1 | 10/2005 | Carr et al. |
| 2006/0040297 | A1 | 2/2006 | Leamon et al. |
| 2006/0054503 | A1 | 3/2006 | Pamula et al. |
| 2006/0127920 | A1* | 6/2006 | Church .......... C12Q 1/6846 435/6.16 |
| 2006/0127926 | A1 | 6/2006 | Belshaw et al. |
| 2006/0194214 | A1* | 8/2006 | Church .......... C12Q 1/6813 435/6.16 |
| 2006/0275771 | A1 | 12/2006 | Suzuki et al. |
| 2007/0122817 | A1* | 5/2007 | Church .......... C12Q 1/6844 435/6.16 |
| 2007/0269870 | A1* | 11/2007 | Church .......... C12Q 1/6844 435/91.2 |
| 2007/0281309 | A1 | 12/2007 | Kong et al. |
| 2008/0053205 | A1 | 3/2008 | Pollack et al. |
| 2008/0105829 | A1 | 5/2008 | Fads et al. |
| 2008/0203502 | A1 | 8/2008 | Heller et al. |
| 2009/0087840 | A1 | 4/2009 | Baynes et al. |
| 2010/0015614 | A1 | 1/2010 | Beer et al. |
| 2011/0172127 | A1 | 7/2011 | Jacobson et al. |
| 2014/0309119 | A1 | 10/2014 | Jacobson et al. |

FOREIGN PATENT DOCUMENTS

| | | |
|---|---|---|
| WO | WO-9320092 A1 | 10/1993 |
| WO | WO-9942813 A1 | 8/1999 |
| WO | WO-0188173 A2 | 11/2001 |
| WO | WO-03040410 A1 | 5/2003 |
| WO | WO-03046223 A1 | 6/2003 |
| WO | WO-03054232 A2 | 7/2003 |
| WO | WO-03064026 A1 | 8/2003 |
| WO | WO-03064027 A2 | 8/2003 |
| WO | WO-03064699 A2 | 8/2003 |
| WO | WO-03065038 A2 | 8/2003 |
| WO | WO-03066212 A2 | 8/2003 |
| WO | WO-03100012 A2 | 12/2003 |
| WO | WO-2004024886 A2 | 3/2004 |
| WO | WO-2004029586 A1 | 4/2004 |
| WO | WO-2004031351 A2 | 4/2004 |
| WO | WO-2004031399 A2 | 4/2004 |
| WO | WO-2004090170 A1 | 10/2004 |
| WO | WO-2005059096 A2 | 6/2005 |
| WO | WO-2005071077 A1 | 8/2005 |
| WO | WO-2006044956 A1 | 4/2006 |
| WO | WO-2006076679 A1 | 7/2006 |
| WO | WO-2007136736 A2 | 11/2007 |
| WO | WO-2008024319 A2 | 2/2008 |
| WO | WO-2011056872 A2 | 5/2011 |
| WO | WO-2011066185 A1 | 6/2011 |
| WO | WO-2011066186 A1 | 6/2011 |

OTHER PUBLICATIONS

Aslanzadeh, Brief Review : Preventing PCR Amplification Carry-over Contamination in a Clinical Laboratory. Annals of Clinical & Laboratory Science 34(4):389 (2004).

Beer, N., et al., "On-chip, real time single-copy polymerase chain reaction in picoliter droplets," Analytical Chemistry, 79(22):8471-8475, (Nov. 15, 2007).

Bennett, S., "Solexa Ltd.," Pharmacogenomics, 5(4):433-8, (Jun. 2004).

Binkowski, B., et al. "Correcting errors in synthetic DNA through consensus shuffling," Nucleic Acids Research, 33(6):1-8, (2005).

Boal, J., et al. "Cleavage of oligodeoxyribonucleotides from controlled-pore glass supports and their rapid deprotection by gaseous amines," NAR, 24(15):3115-3117, (1996).

Cho et al. Creating, Transporting, Cutting, and Merging Liquid Droplets by Electrowetting-Based Actuation for Digital Microfluidic Circuits. Journal of Microelectromechanical systems 12(1) : 70 (2003).

Duggan, D., et al., "Expression profiling using cDNA microarrays," Nat. Genet. 21:10-14, (Jan. 1999).

Ellson, Picoliter: enabling precise transfer of nanoliter and picoliter volumes. Drug Discovery Today 7(5 Suppl.) : S32 (2002).

Fidalgo, L., et al., "Surface induced droplet fusion in microfluidic devices," Lab on Chip, 7(8)984-986, (2007).

Fodor, S., et al., "Light-directed, spatially addressable parallel chemical synthesis," Science, 251(4995):767-773, (Feb. 15, 1991).

Greenberg, M. and Gilmore, J., "Cleavage of oligonucleotides from solid-phase support using o-nitrobenzyl photochemistry," J. of Org. Chem., 59(4):746-753, (Feb. 1994).

Griffith, E. and Akella, S., "Coordinating Multiple Droplets in Planar Array Digital Microfluidic Systems," International Journal of Robotics Research, 24(11):933-949, (Nov. 2005).

Gulati S. et al. "Opportunities for microfluidic technologies in synthetic biology." Journal of the Royal Society, Interface/ The Royal Society, vol. 6, Suppl. 4, S493-S506, 2009.

Haeberle, S. and Zengerle, R., "Microfluidic platform of lab-on chip applications," Lab on Chip, 7(9):1094-1110, (2007).

Hardy, P., et al., "Reagents for the preparation of two oligonucleotides per synthesis (TOPS.TM.)," Nucleic Acids Research, 22(15):2998-3004, (1994).

Holmes, C., "Model studies for new o-nitrobenzyl photolabile linkers: substituent effects on the rates of photochemical cleavage," J. of Org. Chem., 62(8):2370-2380, (Apr. 18, 1997).

Hyman, E., "A new method of sequencing DNA," Analytical Biochemistry, 174(2):423-436, (Nov. 1, 1988).

International Search Report based on International Application No. PCT/US2009/055267 dated Jun. 7, 2010.

Kahl, J., et al. "Solution-Phase Bioconjugate Synthesis Using Protected Oligonucleotides Containing 3'-Alkyl Carboxylic Acids," J. of Org. Chem., 64(2):507-510, (1999).

Kahl, J., et al., "High-Yielding Method for On-Column Derivatization of Protected Oligodeoxy-nucleotides and Its Application to the Convergent Synthesis of 5',3'-Bis-conjugates," J. of Org. Chem., 63(15):4870-4871, (Jul. 8, 1998).

Kelly, B., et al., "Miniaturizing chemistry and biology in microdroplets," Chem. Commun., 1773-1788, (2007).

Kong, D., et al., "Parallel gene synthesis in microfluidic device," Nucleic Acids Research, 35(8):e61 (9 pages), (2007).

(56) References Cited

OTHER PUBLICATIONS

Kumaresan et al., High-Throughput Single Copy DNA Amplification and Cell Analysis in Engineered Nanoliter Droplets, Analytical Chemistry, 80:3522 (2008).
Lashkari et al., An automated multiplex oligonucleotide synthesizer: development of high-throughput, low-cost DNA synthesis. PNAS 92 : 7912 (1995).
Leamon, J., et al., "A massively parallel PicoTiterPlate.TM. based platform for discrete picoliter-scale polymerase chain reactions," Electrophoresis, 24(21):3769-3777, (Nov. 2003).
Liu, Y., et al., "DNA ligation of ultramicrovolume using EWOD microfluidic system with coplanar electrodes: DNA ligation of ultramicrovolume using EWOD microfluidic systems," Journal of Micromechanics & Microengineering, Institute of Physics,18(4):45017 (7 pages), (Apr. 2008).
Margulies, M., et al., "Genome sequencing in microfabricated high-density picolitre reactors," Nature, 437(7057):376-80, (Sep. 15, 2005).
McGall, G., et al., "Light-directed synthesis of high-density oligonucleotide arrays using semiconductor photoresists," Proc. Natl. Acad. Sci. U.S.A, 93:13555-13560, (Nov. 1996).
Metzker, M. Emerging technologies in DNA sequencing Genome Research 15 :1767 (2005).
Metzker, M., et al., "Termination of DNA synthesis by novel 3'-modifieddeoxyribonucleoside 5'-triphosphates," NAR, 22(20):4259-4267, (1994).
Mitra, R., et al., "Fluorescent in situ sequencing on polymerase colonies," Analytical Biochemistry, 320:55-65, (2003).
Moffitt et al., Recent Advances in Optical Tweezers. Annual Review of Biochemistry 77 :205 (Feb. 2008).
Neuman et al., Optical Trapping. Review of Scientific Instruments 75(9) : 2787 (2004).
Pon., R. "Solid-phase supports for oligonucleotide synthesis," Methods Mol. Biol., 20:465-496, (1993).
Randegger et al., Real-time PCR and melting curve analysis for reliable and rapid detection of SHV extended-spectrum beta-lactamases. Antimicrobial Agents and Chemotherapy 45 (6) : 1730 (2001).
Richmond, K., et al., "Amplification and assembly of chip-eluted DNA (AACED): a method of high-throughput gene-synthesis," Nucleic Acids Research, 32(17):5011-5018, (Jan. 1, 2004).
Schaerli, Y., et al., "Continuous-Flow polymerase Chain reaction of single-copy DNA Micorfluidic Microdroplets," Anal. Chem., 81: 302-306, (2009).
Seo, T., et al., "Four-color DNA sequencing by synthesis on a chip using photocleavable fluorescent nucleotides," PNAS, 102(17):5926-5933, (Apr. 26, 2005).
Shabarova, Z., et al., "Chemical ligation of DNA: the first non-enzymatic assembly of a biologically active gene," Nucl. Acids Res., 19(15):4247-4251, (1991).
Shendure, J., et al., "Accurate Multiplex Polony Sequencing of an Evolved Bacterial Genome," Science, 309:1728-1732, (Sep. 9, 2005).
Stekel, D., "Microarrays: Making Them and Using Them in Microarray Bioinformatics," Cambridge University Press, 2003, (10 pages).
Stemmer et al., Single-step assembly of a gene and entire plasmid from large numbers of oligodeoxyribonucleotides. Gene 164: 49 (1995).
Teh, S-Y, et al., "Droplet microfluidics," Lab on Chip, 8(2), (2008).
Tian, J., et al., "Accurate multiplex gene synthesis from programmable DNA microchips," Nature, 432(7020):1050-1054, (Dec. 23-30, 2004).
Venkatesan, H. and Greenberg, M.,"Improved Utility of Photolabile Solid Phase Synthesis Supports for the Synthesis of Oligonucleotides Containing 3'-Hydroxyl Termini," J. of Org. Chem., 61:525-529, (Jan. 26, 1996).
Verma, S. and Eckstein, F., "Modified Oligonucleotides: Synthesis and Strategy for Users," Annu. Rev. Biochem., 67:99-134, (1998).
Whitesides. G., The origins and the future of microfluidics, Nature, 442: 368 (2006).
Xiong et al., PCR-based accurate synthesis of long DNA sequences. Nature Protocols 1 (2) : 791 (2006).
Xu, Y. and Kool, E., "A Novel 5'-Iodonucleoside allows efficient nonenzymatic ligation of single-stranded and duplex DNAs" Tetrahedron Letter, 38(32):5595-5598, (Aug. 11, 1997).
Xu, Y. and Kool, E., "High sequence fidelity in a non-enzymatic DNA autoligation reaction" Nuc. Acids Res., 27(3):875-881, (1999).
Xu, Y., et al., "Nonenzymatic autoligation in direct three-color detection of RNA and DNA point mutations" Nature Biotech., 19:148-52, (Feb. 2001).
Zhang, C., et al., "PCR microfluidic devices for DNA amplification," Biotechnology Advances, 24(3):243-284, 2006.
Zhou, X., et al., "Microfluidic PicoArray synthesis of oligodeoxynucleotides and simultaneous assembling of multiple DNA sequences" Nucleic Acids Research, 32(18):5409-5417, (2004).
Hayden et al., Gene synthesis by serial cloning of oligonucleotides. DNA. Oct. 1988;7(8):571-7.

\* cited by examiner

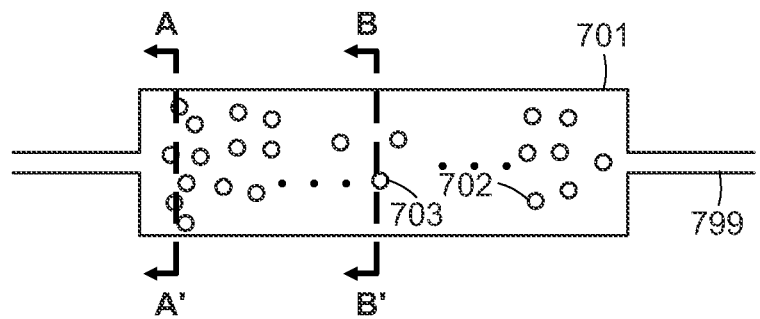
FIG. 5A
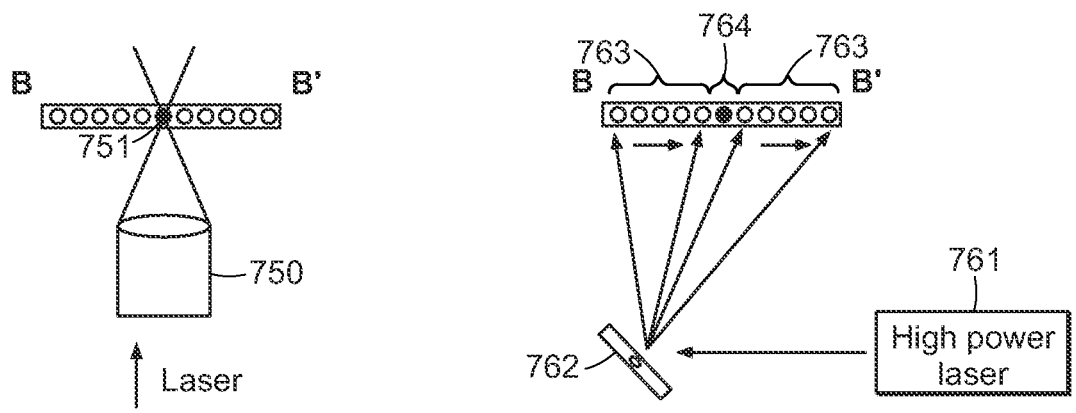
FIG. 5B
FIG. 5C
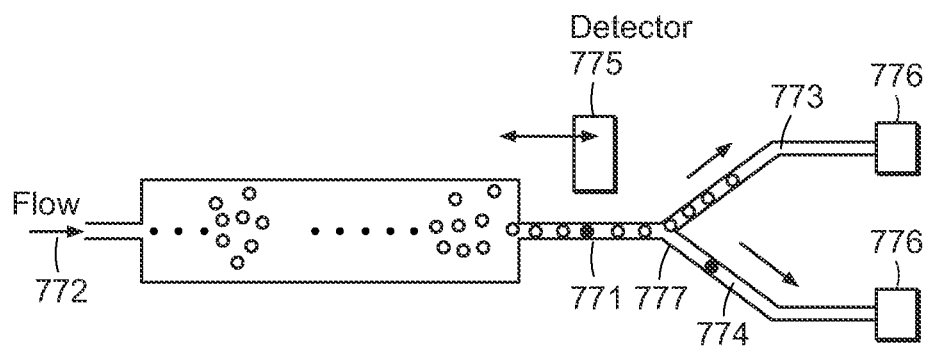
FIG. 5D

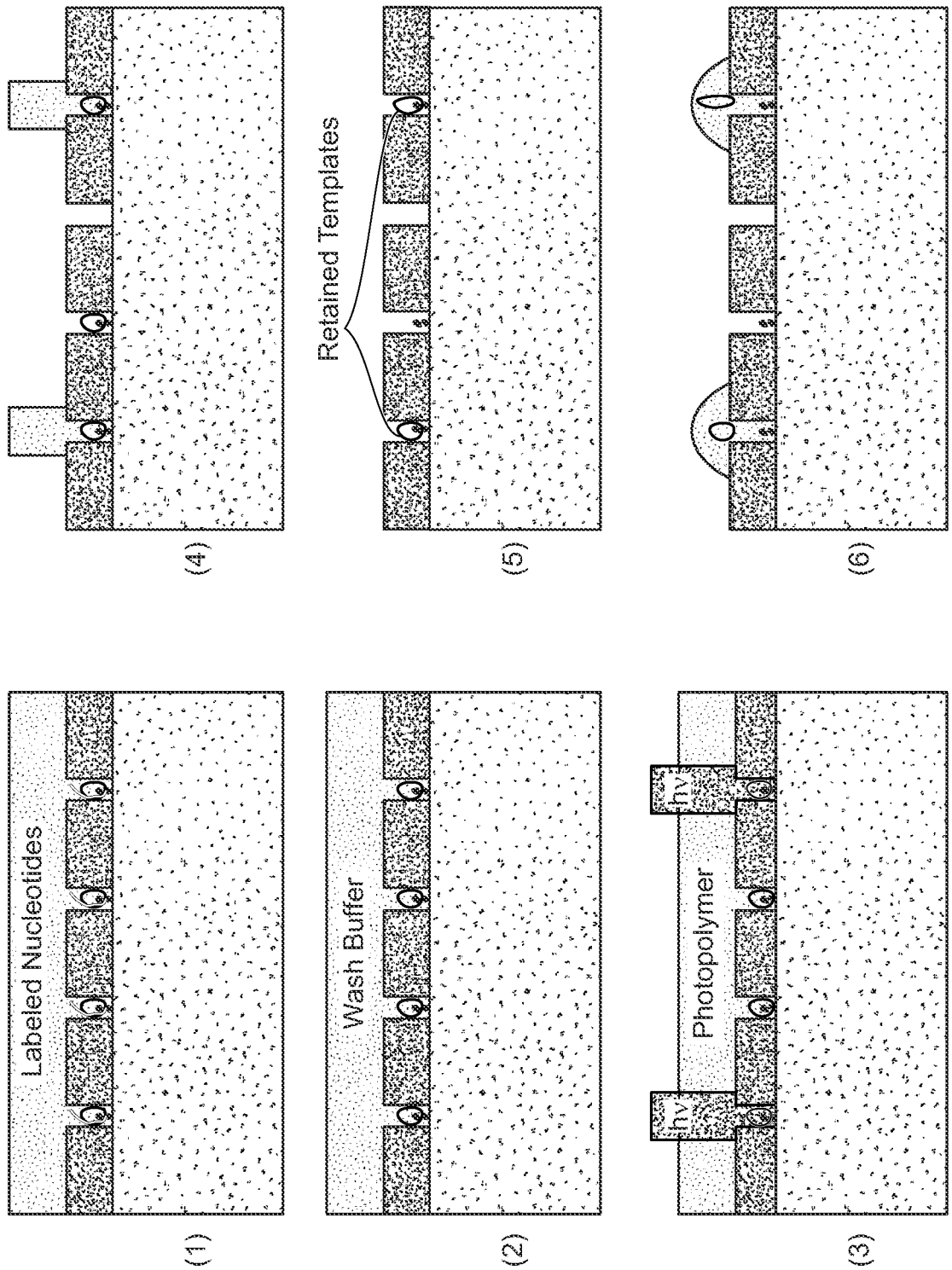

METHODS AND DEVICES FOR HIGH FIDELITY POLYNUCLEOTIDE SYNTHESIS

RELATED APPLICATIONS

The present application claims the benefit of U.S. patent application Ser. No. 14/317,082, filed Jun. 27, 2014, which claims the benefit of U.S. patent application Ser. No. 13/060,178, filed Mar. 29, 2011, now U.S. Pat. No. 8,808,986, which is a National Stage Entry of Patent Cooperation Treaty Application No. PCT/US2009/055267, filed Aug. 27, 2009, which claims priority to United States Provisional Application Nos. 61/092,309, filed Aug. 27, 2008, and 61/235,677, filed Aug. 20, 2009, the entire disclosure of each of which is herein incorporated by reference.

STATEMENT REGARDING FEDERALLY SPONSORED RESEARCH

This invention was made with United States Government support under the cooperative agreement number 70NANB7H7034N awarded by the National Institute of Standards and Technology. The United States Government has certain rights in the invention.

FIELD OF THE INVENTION

Methods and devices provided herein relate to the assembly of high fidelity nucleic acid and nucleic acid libraries having a predefined sequence using microvolume reactions. More particularly, methods and devices are provided for polynucleotide synthesis, error filtration, hierarchical assembly, and sequence verification on a solid support. In some embodiments, picoliter and sub picoliter dispensing and droplet-moving technologies are applied to access and manipulate the oligonucleotides on DNA microarrays.

BACKGROUND

Using the techniques of recombinant DNA chemistry, it is now common for DNA sequences to be replicated and amplified from nature and then disassembled into component parts. As component parts, the sequences are then recombined or reassembled into new DNA sequences. However, reliance on naturally available sequences significantly limits the possibilities that may be explored by researchers. While it is now possible for short DNA sequences to be directly synthesized from individual nucleosides, it has been generally impractical to directly construct large segments or assemblies of polynucleotides, i.e., DNA sequences larger than about 400 base pairs. Furthermore, chemically synthesized oligonucleotides may have an error rate (deletions at a rate of 1 in 100 bases and mismatches and insertions at about 1 in 400 bases) exceeding the error rate obtainable through enzymatic means of replicating an existing nucleic acid (e.g., PCR). Therefore, there is an urgent need for new technology to produce high-fidelity polynucleotides.

Oligonucleotide synthesis can be performed through massively parallel custom syntheses on microchips (Zhou et al. (2004) Nucleic Acids Res. 32:5409; Fodor et al. (1991) Science 251:767). However, current microchips have very low surface areas and hence only small amounts of oligonucleotides can be produced. When released into solution, the oligonucleotides are present at picomolar or lower concentrations per sequence, concentrations that are insufficiently high to drive bimolecular priming reactions efficiently. Current methods for assembling small numbers of variant nucleic acids cannot be scaled up in a cost-effective manner to generate large numbers of specified variants. As such, a need remains for improved methods and devices for increasing throughput and cost-efficiency in high-fidelity gene assembly and the like.

SUMMARY

Aspects of the technology provided herein relate to devices for preparing and/or assembling high fidelity polymers. Provided herein are devices and methods for processing nucleic acid assembly reactions and assembling nucleic acids. It is an object of this invention to provide practical, economical methods of synthesizing custom polynucleotides. It is a further object to provide a method of producing synthetic polynucleotides that have lower error rates than synthetic polynucleotides made by methods known in the art.

In one aspect, the invention provides for methods for assembling a polynucleotide having a predefined sequence from a plurality of different oligonucleotides, According to one aspect, the methods of the invention comprise providing a plurality of single-stranded template oligonucleotides on a support, wherein each of the plurality of template oligonucleotides comprises a predefined sequence and includes a primer binding site; generating a complementary oligonucleotide for each of the plurality of template oligonucleotides by enzyme-catalyzed synthesis within a first stage or primary droplet, thereby producing a plurality of double-stranded oligonucleotides; releasing the complementary oligonuceotides from the double-stranded oligonucleotides into the primary droplet; combining at least a first and second primary droplets, thereby forming a second stage or secondary droplet, wherein the first primary droplet includes a released oligonucleotide that comprises a portion that is complementary to a portion of a released or template oligonucleotide from the second primary droplet; and exposing the secondary droplet to conditions suitable for hybridization and ligation, polymerase extension, or polymerase extension and ligation to assemble a double-stranded polynucleotide having a predefined sequence.

In some embodiments methods of assembling libraries containing nucleic acids having predetermined sequence variations are provided. Assembly strategies provided herein can be used to generate very large libraries representative of many different nucleic acid sequences of interest.

Methods and devices for analyzing nucleic acid assembly reactions are also provided herein. In some embodiments, the analysis of the nucleic acid assembly reactions comprises sequencing. In some embodiments provided herein, certain microfluidic device configurations may be useful to amplify, assemble, sequence, isolate and/or purify one or more nucleic acid and/or subassemblies during a nucleic acid assembly procedure. In some embodiments of the technology provided herein, hierarchical and/or sequential assembly is performed. In a preferred embodiment, the methods use hierarchical assembly of two or more oligonucleotides or two or more subassemblies polynucleotide fragments at a time. In a further embodiment, the methods use sequential reaction to assemble larger nucleic acids. Oligonucleotides and/or subassembly fragments may be combined and processed more rapidly and reproducibly to increase the throughput rate of the assembly.

In some embodiments of the technology provided herein, droplets, as isolated reaction microvolumes, are used for parallel reactions. Methods and devices provided herein may involve small assembly reaction volumes. For example, reaction volumes of between about 0.5 pL and about 500 nL may be used. However, smaller or larger volumes may be used. In some embodiments, a mechanical wave actuated dispenser may be used for transferring volumes of less than 100 nL, less than 10 nL, less than 5 nL, less than 100 pL, less than 10 pL, or about 0.5 pL or less. In some embodiments, the mechanical wave actuated dispenser can be a piezoelectric inkjet device or an acoustic liquid handler.

In some embodiments, the throughput rate of an assembly reaction may be increased by using highly precise droplets dispensing technology.

In some embodiments, a piezoelectric inkjet device or an acoustic liquid handler may be used to prepare mixtures of reagents or biomolecules (e.g., oligonucleotides) for one or more reactions onto a solid substrate or microfluidic substrate. In some embodiments, piezoelectric inkjet or acoustic liquid delivery techniques may be used to introduce samples and/or reagents onto a substrate. In some embodiments, samples may be oligonucleotides or polynucleotides. In some embodiments, reagents may be enzymes (e.g. polymerase, ligase, etc.), buffer, dNTPs, primers, etc. or any combination thereof.

In one aspect, methods and devices to amplify oligonucleotides or polynucleotides in a reaction microvolume or droplet on a solid support are provided. In some embodiments, oligonucleotides are attached, spotted, immobilized, supported or synthesized on a solid support. In some embodiments, the oligonucleotides sequences are flanked with primer binding sites. In preferred embodiments, the oligonucleotides are amplified before being assembled. Oligonucleotides may be amplified before or after being detached from the solid support and/or eluted in a droplet. In some embodiments, the oligonucleotides are amplified on the solid support using a scanning laser or a spatial optical modulator (e.g., a digital micromirror device or DMD) capable of individually modulating the temperature of a droplet.

In one aspect, methods and devices for isolating nucleic acid intermediates during a polymerase-mediated, a ligation-mediated, or polymerase and ligation-mediated assembly procedure are provided. Certain assembly steps may generate a mixture of nucleic acids that include a variety of incorrectly assembled nucleic acids.

An assembly reaction mixture may be processed through sequencing and/or selective isolation station arranged to segregate or otherwise group subject molecules based on sequence. In preferred embodiments, the assembly reaction mixture or one or more of its components are prepared through the action of an acoustic liquid handler or a mechanical wave actuated dispenser (e.g., an acoustic droplet ejector or a piezoelectric inkjet device). In some embodiments, mechanical wave liquid delivery technology may be used to directly deposit one or more reagents or a reaction mixture directly onto a solid substrate. In some embodiments, the reaction mixture may be generated on the substrate on an appropriate reaction location. In some embodiments, reaction mixtures (e.g. oligonucleotides or subassemblies) in distinct droplets may be merged together by dispensing additional liquid droplets in between or around the original droplets using an acoustic liquid handling technique (e.g., via the action of a droplet ejector). In some embodiments, the correctly assembled nucleic acids are removed from the substrate using laser tweezer methods or FACS like methods. Alternatively, incorrectly assembled or undesired product can be laser ablated. In some embodiments, further assembly steps are performed on the same substrate to assemble larger nucleic acids.

In some embodiments, a sequencing platform that is integrated into the devices provided herein. In some embodiments, a sequencing station is used to process the products from each different assembly reactions. Certain microfluidic device configurations may be adapted sequencing and/or selective isolation operations within an integrated (e.g., automated) assembly procedure. Microfluidic devices may be configured to isolate and/or sequence a plurality of assembly reactions rapidly and efficiently. In some embodiments, a plurality of reactions may be processed in parallel. Accordingly, the technology provided herein is useful to increase the rate, yield, and/or precision of nucleic acid assembly. This can decrease the cost and/or delivery time for manufacturing a nucleic acid product.

Accordingly, devices and methods for enhancing the assembly of target nucleic acids or intermediates thereof are provided herein. In some embodiments, an assembled target nucleic acid may be amplified, sequenced, isolated and/or cloned after it is made. In some embodiments, a host cell may be transformed with the assembled target nucleic acid. The target nucleic acid may be integrated into the genome of the host cell. In some embodiments, the target nucleic acid may encode a polypeptide. The polypeptide may be expressed (e.g., under the control of an inducible promoter). The polypeptide may be isolated or purified. A cell transformed with an assembled nucleic acid may be stored, shipped, and/or propagated (e.g., grown in culture).

The invention further provides for methods for synthesizing a plurality of oligonucleotides having a predefined sequence. According to one embodiment, the method comprises providing a plurality of support-bound template oligonucleotides in a solution comprising a primer, a polymerase and nucleotides, wherein each of the plurality of template oligonucleotides comprises a predefined sequence and includes a primer binding site, and wherein the primer comprises at least one nuclease recognition site; exposing the plurality of template oligonucleotides to conditions suitable for primer hybridization and polymerase extension, thereby extending the primers to produce a complementary oligonucleotide for each of the plurality of template oligonucleotides; releasing the complementary oligonuceotides; exposing the complementary oligonucleotides to a nuclease under conditions suitable for the nuclease to bind to the nuclease recognition site on the primer and cleave the primer from complementary oligonucleotide; and exposing the complementary and template oligonucleotides to conditions suitable for hybridization; thereby to produce a plurality of partially double-stranded oligonucleotides. In one embodiment, methods of the invention further comprise washing the plurality of partially double-stranded oligonucleotides and releasing the complementary oligonucleotides. Aspects of the invention also contemplate using a primer comprising at least two nuclease recognition sites, and the step of exposing the cleaved primer to a second nuclease under conditions suitable for the second nuclease to bind to the primer and subject the primer to further cleavage.

Other features and advantages of the devices and methods provided herein will be apparent from the following detailed description, and from the claims. The claims provided below are hereby incorporated into this section by reference. The various embodiments described herein can be complimentary and can be combined or used together in a manner understood by the skilled person in view of the teachings contained herein.

BRIEF DESCRIPTION OF THE FIGURES

FIG. 5A illustrates non-limiting example of method and devices to capture desired product comprising a microfluidics reaction chamber (701) for sequencing reaction; individual sequencing reaction sites, containing undesirable material (702), reaction site containing desired population (703), an outlet (exit) (799) of the chamber, a Laser. FIG. 5B illustrates a non-limiting example of device using an optical tweezer system and comprising a lens system (750) to implement optical tweezers and a location of the focus of an optical tweezers system (751). FIG. 5C illustrates a non-limiting example using a laser device to ablate undesired products comprising a high power laser (761) to generate optical energy, a scanning setup (762) to control the position of the energy beam at specific location (763). FIG. 5D illustrates a non-limiting example to track desired product suing a vision system comprising: Outlet of the reaction chamber (701); 772: An input flow to induce the contents of 701 to exit at 771; 773: An offshoot channel that contains the undesirable material; 774: An offshoot channel that contains the desirable material; 775: A detector that determines fixates on the desired products, and tracking its position; 776: Flow controllers to direct the sorting process; and 777: Sorting junction. FIG. 5E illustrates a method to achieve "selective isolation" that can involve the utilization of photopolymers to retain and trap desirable products.

DETAILED DESCRIPTION OF THE INVENTION

Figure 1A:
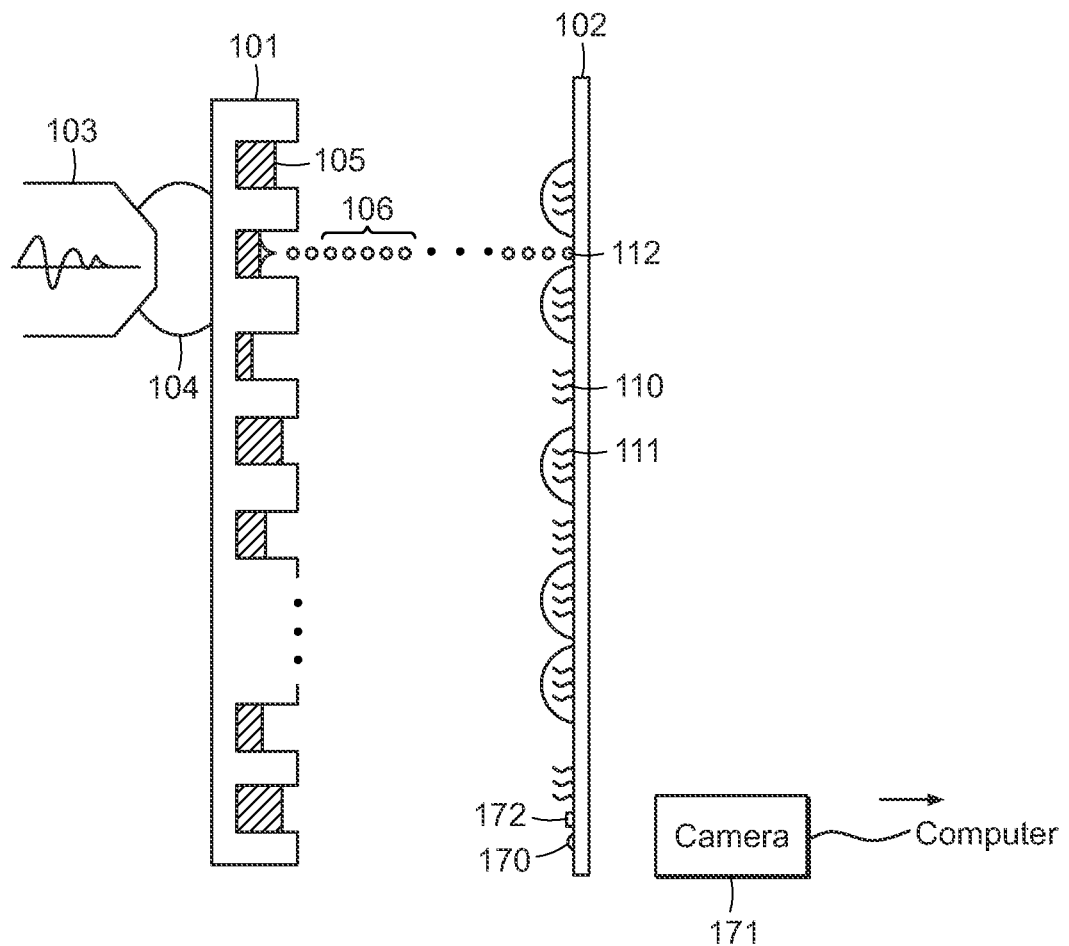
FIG. 1A illustrates an embodiment of the device comprising a source well plate (101), containing the reagents for reactions, a solid support (102), with solid-attached surface or supported molecules, a transducer (103), a coupling fluid (104), reagents (105) inside a well, solid attached or surface supported molecules (110), surface droplets (111) formed by the dispensed droplets (106), a "merge" droplet (112) dispensed between two surface droplets (111), a surface droplet (170) dispensed for the purpose of alignment of the droplet to the solid attached molecules (111), an electronics camera (171) and used to provide physical registration (positioning) and a surface mark (172) fixed on the solid support (102).

Provided herein are apparatuses for preparing and/or assembling polymers. In some embodiments, devices and methods for processing nucleic acid assembly reactions and assembling nucleic acids are provided herein. As used herein the term "nucleic acid" "polynucleotide" and "oligonucleotide" are used interchangeably and refers to polymeric form of nucleotides, either ribonucleotides and/or deoxyribonucleotides or a modified form of either type of nucleotides. The term should be understood to include equivalents, analogs of either RNA or DNA made from nucleotide analogs and as applicable to the embodiment being described, single stranded or double stranded polynucleotides.

In some embodiments, methods of assembling libraries containing nucleic acids having predetermined sequence variations are provided herein. Assembly strategies provided herein can be used to generate very large libraries representative of many different nucleic acid sequences of interest. In some embodiments, libraries of nucleic acid are libraries of sequence variants. Sequence variants may be variants of a single naturally-occurring protein encoding sequence. However, in some embodiments, sequence variants may be variants of a plurality of different protein-encoding sequences.

Accordingly, one aspect of the technology provided herein relates to the design of assembly strategies for preparing precise high-density nucleic acid libraries. Another aspect of the technology provided herein relates to assembling precise high-density nucleic acid libraries. Aspects of the technology provided herein also provide precise high-density nucleic acid libraries. A high-density nucleic acid library may include more that 100 different sequence variants (e.g., about $10^2$ to $10^3$; about $10^3$ to $10^4$; about $10^4$ to $10^5$; about $10^5$ to $10^6$; about $10^6$ to $10^7$; about $10^7$ to $10^8$; about $10^8$ to $10^9$; about $10^9$ to $10^{10}$; about $10^{10}$ to $10^{11}$; about $10^{11}$ to $10^{12}$; about $10^{12}$ to $10^{13}$; about $10^{13}$ to $10^{14}$; about $10^{14}$ to $10^{15}$; or more different sequences) wherein a percentage of the different sequences are specified sequences as opposed to random sequences (e.g., more than about 10, 15, 20, 25, 30, 35, 40, 45, 50, 55, 60, 65, 70, 75, 80, 85, 90, 91, 92, 93, 94, 95, 96, 97, 98, 99% of the sequences are predetermined sequences of interest).

Provided herein are microfluidic devices and systems for preparing and/or assembling polymers. One aspect of the technology provided herein is generally directed to the synthesis of long polymers and biopolymers such as nucleic acids. Aspects of the technology provided herein may be useful for increasing the accuracy, yield, throughput, and/or cost efficiency of nucleic acid assembly reactions.

In some embodiments, the assembly procedure may include several parallel and/or sequential reaction steps in which a plurality of different nucleic acids or oligonucleotides are synthesized or immobilized, amplified, filtered, and combined for assembly (e.g., by extension or ligation as described herein) to generate a longer nucleic acid product to be used for further assembly, cloning, or other applications. Assembly strategies provided herein can be used to generate very large libraries representative of many different nucleic acid sequences of interest.

In some embodiments of the technology provided herein, immobilized or surface-supported oligonucleotides or polynucleotides are used as a source of material. In various embodiments, the methods described herein uses oligonucleotides, their sequence being determined based on the sequence of the final polynucleotides constructs to be synthesized. In one embodiment, "oligonucleotides" are short nucleic acid molecules. For example, oligonucleotides may be from 10 to about 300 nucleotides, from 20 to about 400 nucleotides, from 30 to about 500 nucleotides, from 40 to about 600 nucleotides, or more than about 600 nucleotides long. However shorter or longer oligonucleotides may be used. Oligonucleotides may be designed to have different length. In some embodiments, the sequence of the polynucleotide construct may be divided up into a plurality of shorter sequences that can be synthesized in parallel and assembled into a single or a plurality of desired polynucleotide constructs using the methods described herein. In certain embodiments, the oligonucleotides are designed to provide the full sense and antisense strands of the polynucleotide construct. After hybridization of the plus and minus strand oligonucleotides, two double stranded oligonucleotides are subjected to ligation or polymerization in order to form a first subassembly product. Subassembly products are then subjected to ligation or polymerization to form a larger DNA or the full DNA sequence.

Ligase-based assembly techniques may involve one or more suitable ligase enzymes that can catalyze the covalent linking of adjacent 3' and 5' nucleic acid termini (e.g., a 5' phosphate and a 3' hydroxyl of nucleic acid(s) annealed on a complementary template nucleic acid such that the 3' terminus is immediately adjacent to the 5' terminus). Accordingly, a ligase may catalyze a ligation reaction between the 5' phosphate of a first nucleic acid to the 3' hydroxyl of a second nucleic acid if the first and second nucleic acids are annealed next to each other on a template nucleic acid). A ligase may be obtained from recombinant or natural sources. A ligase may be a heat-stable ligase. In some embodiments, a thermostable ligase from a thermophilic organism may be used. Examples of thermostable DNA ligases include, but are not limited to: Tth DNA ligase (from *Thermus thermophilus*, available from, for example, Eurogentec and GeneCraft); Pfu DNA ligase (a hyperthermophilic ligase from *Pyrococcus furiosus*); Taq ligase (from *Thermus aquaticus*), any other suitable heat-stable ligase, or any combination thereof. In some embodiments, one or more lower temperature ligases may be used (e.g., T4 DNA ligase). A lower temperature ligase may be useful for shorter overhangs (e.g., about 3, about 4, about 5, or about 6 base overhangs) that may not be stable at higher temperatures.

Non-enzymatic techniques can be used to ligate nucleic acids. For example, a 5'-end (e.g., the 5' phosphate group) and a 3'-end (e.g., the 3' hydroxyl) of one or more nucleic acids may be covalently linked together without using enzymes (e.g., without using a ligase). In some embodiments, non-enzymatic techniques may offer certain advantages over enzyme-based ligations. For example, non-enzymatic techniques may have a high tolerance of non-natural nucleotide analogues in nucleic acid substrates, may be used to ligate short nucleic acid substrates, may be used to ligate RNA substrates, and/or may be cheaper and/or more suited to certain automated (e.g., high throughput) applications.

Non-enzymatic ligation may involve a chemical ligation. In some embodiments, nucleic acid termini of two or more different nucleic acids may be chemically ligated. In some embodiments, nucleic acid termini of a single nucleic acid may be chemically ligated (e.g., to circularize the nucleic acid). It should be appreciated that both strands at a first double-stranded nucleic acid terminus may be chemically ligated to both strands at a second double-stranded nucleic acid terminus. However, in some embodiments only one strand of a first nucleic acid terminus may be chemically ligated to a single strand of a second nucleic acid terminus. For example, the 5' end of one strand of a first nucleic acid terminus may be ligated to the 3' end of one strand of a second nucleic acid terminus without the ends of the complementary strands being chemically ligated.

Accordingly, a chemical ligation may be used to form a covalent linkage between a 5' terminus of a first nucleic acid end and a 3' terminus of a second nucleic acid end, wherein the first and second nucleic acid ends may be ends of a single nucleic acid or ends of separate nucleic acids. In one aspect, chemical ligation may involve at least one nucleic acid substrate having a modified end (e.g., a modified 5' and/or 3' terminus) including one or more chemically reactive moieties that facilitate or promote linkage formation. In some embodiments, chemical ligation occurs when one or more nucleic acid termini are brought together in close proximity (e.g., when the termini are brought together due to annealing between complementary nucleic acid sequences). Accordingly, annealing between complementary 3' or 5' overhangs (e.g., overhangs generated by restriction enzyme cleavage of a double-stranded nucleic acid) or between any combination of complementary nucleic acids that results in a 3' terminus being brought into close proximity with a 5' terminus (e.g., the 3' and 5' termini are adjacent to each other when the nucleic acids are annealed to a complementary template nucleic acid) may promote a template-directed chemical ligation. Examples of chemical reactions may include, but are not limited to, condensation, reduction, and/or photochemical ligation reactions. It should be appreciated that in some embodiments chemical ligation can be used to produce naturally occurring phosphodiester internucleotide linkages, non-naturally-occurring phosphamide pyrophosphate internucleotide linkages, and/or other non-naturally-occurring internucleotide linkages.

In some embodiments, the process of chemical ligation may involve one or more coupling agents to catalyze the ligation reaction. A coupling agent may promote a ligation reaction between reactive groups in adjacent nucleic acids (e.g., between a 5'-reactive moiety and a 3'-reactive moiety at adjacent sites along a complementary template). In some embodiments, a coupling agent may be a reducing reagent (e.g., ferricyanide), a condensing reagent such (e.g., cyanoimidazole, cyanogen bromide, carbodiimide, etc.), or irradiation (e.g., UV irradiation for photo-ligation).

In some embodiments, a chemical ligation may be an autoligation reaction that does not involve a separate coupling agent. In autoligation, the presence of a reactive group on one or more nucleic acids may be sufficient to catalyze a chemical ligation between nucleic acid termini without the addition of a coupling agent (see, for example, Xu et al., (1997) Tetrahedron Lett. 38:5595-8). Non-limiting examples of these reagent-free ligation reactions may involve nucleophilic displacements of sulfur on bromoacetyl, tosyl, or iodo-nucleoside groups (see, for example, Xu et al., (2001) Nat. Biotech. 19:148-52). Nucleic acids containing reactive groups suitable for autoligation can be prepared directly on automated synthesizers (see, for example, Xu et al., (1999) Nuc. Acids Res. 27:875-81). In some embodiments, a phosphorothioate at a 3' terminus may react with a leaving group (such as tosylate or iodide) on a thymidine at an adjacent 5' terminus. In some embodiments, two nucleic acid strands bound at adjacent sites on a complementary target strand may undergo auto-ligation by displacement of a 5'-end iodide moiety (or tosylate) with a 3'-end sulfur moiety. Accordingly, in some embodiments the product of an autoligation may include a non-naturally-occurring internucleotide linkage (e.g., a single oxygen atom may be replaced with a sulfur atom in the ligated product).

In some embodiments, a synthetic nucleic acid duplex can be assembled via chemical ligation in a one step reaction involving simultaneous chemical ligation of nucleic acids on both strands of the duplex. For example, a mixture of 5'-phosphorylated oligonucleotides corresponding to both strands of a target nucleic acid may be chemically ligated by a) exposure to heat (e.g., to 97° C.) and slow cooling to form a complex of annealed oligonucleotides, and b) exposure to cyanogen bromide or any other suitable coupling agent under conditions sufficient to chemically ligate adjacent 3' and 5' ends in the nucleic acid complex.

In some embodiments, a synthetic nucleic acid duplex can be assembled via chemical ligation in a two step reaction involving separate chemical ligations for the complementary strands of the duplex. For example, each strand of a target nucleic acid may be ligated in a separate reaction containing phosphorylated oligonucleotides corresponding to the strand that is to be ligated and non-phosphorylated oligonucleotides corresponding to the complementary strand. The non-phosphorylated oligonucleotides may serve as a template for the phosphorylated oligonucleotides during a chemical ligation (e.g., using cyanogen bromide). The resulting single-stranded ligated nucleic acid may be purified and annealed to a complementary ligated single-stranded nucleic acid to form the target duplex nucleic acid (see, for example, Shabarova et al., (1991) Nucl. Acids Res. 19:4247-51).

In one aspect, a nucleic acid fragment may be assembled in a polymerase mediated assembly reaction from a plurality of oligonucleotides that are combined and extended in one or more rounds of polymerase-mediated extensions. In some embodiments, the oligonucleotides are overlapping oligonucleotides covering the full sequence but leaving single stranded gaps that may be filed in by chain extension. The plurality of different oligonucleotides may provide either positive sequences, negative sequences, or a combination of both positive and negative sequences corresponding to the entire sequence of the nucleic acid fragment to be assembled. In some embodiments, one or more different oligonucleotides may have overlapping sequence regions (e.g., overlapping 5' regions or overlapping 3' regions). Overlapping sequence regions may be identical (i.e., corresponding to the same strand of the nucleic acid fragment) or complementary (i.e., corresponding to complementary strands of the nucleic acid fragment). The plurality of oligonucleotides may include one or more oligonucleotide pairs with overlapping identical sequence regions, one or more oligonucleotide pairs with overlapping complementary sequence regions, or a combination thereof. Overlapping sequences may be of any suitable length. For example, overlapping sequences may encompass the entire length of one or more nucleic acids used in an assembly reaction. Overlapping sequences may be between about 5 and about 500 oligonucleotides long (e.g., between about 10 and 100, between about 10 and 75, between about 10 and 50, about 20, about 25, about 30, about 35, about 45, about 50, etc.). However, shorter, longer, or intermediate overlapping lengths may be used. It should be appreciated that overlaps between different input nucleic acids used in an assembly reaction may have different lengths.

Polymerase-based assembly techniques may involve one or more suitable polymerase enzymes that can catalyze a template-based extension of a nucleic acid in a 5' to 3' direction in the presence of suitable nucleotides and an annealed template. A polymerase may be thermostable. A polymerase may be obtained from recombinant or natural sources. In some embodiments, a thermostable polymerase from a thermophilic organism may be used. In some embodiments, a polymerase may include a 3'→5' exonuclease/proofreading activity. In some embodiments, a polymerase may have no, or little, proofreading activity (e.g., a polymerase may be a recombinant variant of a natural polymerase that has been modified to reduce its proofreading activity). Examples of thermostable DNA polymerases include, but are not limited to: Taq (a heat-stable DNA polymerase from the bacterium *Thermus aquaticus*); Pfu (a thermophilic DNA polymerase with a 3'→5' exonuclease/proofreading activity from *Pyrococcus furiosus*, available from for example Promega); VentR® DNA Polymerase and VentRO (exo-) DNA Polymerase (thermophilic DNA polymerases with or without a 3'→5' exonuclease/proofreading activity from *Thermococcus litoralis*; also known as Th polymerase); Deep VentR® DNA Polymerase and Deep VentR® (exo-) DNA Polymerase (thermophilic DNA polymerases with or without a 3'→5' exonuclease/proofreading activity from *Pyrococcus* species GB-D; available from New England Biolabs); KOD HiFi (a recombinant *Thermococcus kodakaraensis* KODI DNA polymerase with a 3'→5' exonuclease/proofreading activity, available from Novagen,); BIO-X-ACT (a mix of polymerases that possesses 5'-3' DNA polymerase activity and 3'→5' proofreading activity); Klenow Fragment (an N-terminal truncation of *E. coli* DNA Polymerase I which retains polymerase activity, but has lost the 5'→3' exonuclease activity, available from, for example, Promega and NEB); Sequenase™ (T7 DNA polymerase deficient in T-5' exonuclease activity); Phi29 (bacteriophage 29 DNA polymerase, may be used for rolling circle amplification, for example, in a TempliPhi™ DNA Sequencing Template Amplification Kit, available from Amersham Biosciences); TopoTaq (a hybrid polymerase that combines hyperstable DNA binding domains and the DNA unlinking activity of Methanopyrus topoisomerase, with no exonuclease activity, available from Fidelity Systems); TopoTaq HiFi which incorporates a proofreading domain with exonuclease activity; Phusion™ (a *Pyrococcus*-like enzyme with a processivity-enhancing domain, available from New England Biolabs); any other suitable DNA polymerase, or any combination of two or more thereof.

In some embodiments, the polymerase can be a SDP (strand-displacing polymerase; e.g, an SDPe—which is an SDP with no exonuclease activity). This allows isothermal PCR (isothermal extension, isothermal amplification) where duplication of a template takes place at a uniform temperature. As the polymerase (for example, Phi29, Bst) travels along a template it displaces the complementary strand (e.g., created in previous extension reactions). As the displaced DNAs are single stranded, primers can bind at a consistent temperature, removing the need for any thermocycling during amplification, thereby avoiding or decreasing evaporation of the reaction mixture.

It should be appreciated that the description of the assembly reactions in the context of the oligonucleotides is not intended to be limiting. For example, other polynucleotides (e.g. single stranded, double-stranded polynucleotides, restriction fragments, amplification products, naturally occurring polynucleotides, etc.) may be included in an assembly reaction, along with one or more oligonucleotides, in order to generate a polynucleotide of interest.

In some embodiments, the oligonucleotides may comprise universal (common to all oligonucleotides), semiuniversal (common to at least of portion of the oligonucleotides) or individual or unique primer (specific to each oligonucleotide) binding sites on either the 5' end or the 3' end or both. As used herein, the term "universal" primer or primer binding site means that a sequence used to amplify the oligonucleotide is common to all oligonucleotides such that all such oligonucleotides can be amplified using a single set of universal primers. In other circumstances, an oligonucleotide contains a unique primer binding site. As used herein, the term "unique primer binding site" refers to a set of primer recognition sequences that selectively amplifies a subset of oligonucleotides. In yet other circumstances, an oligonucleotide contains both universal and unique amplification sequences, which can optionally be used sequentially.

In some embodiments, primers/primer binding site may be designed to be temporary. For example, temporary primers may be removed by chemical, light based or enzymatic cleavage. For example, primers/primer binding sites may be designed to include a restriction endonuclease cleavage site. In an exemplary embodiment, a primer/primer binding site contains a binding and/or cleavage site for a type IIs restriction endonuclease. In such case, amplification sequences may be designed so that once a desired set of oligonucleotides is amplified to a sufficient amount, it can then be cleaved by the use of an appropriate type IIs restriction enzyme that recognizes an internal type IIs restriction enzyme sequence of the oligonucleotide.

In some embodiments, after amplification, the pool of nucleic acids may be contacted with one or more endonucleases to produce double stranded breaks thereby removing the primers/primer binding sites. In certain embodiments, the forward and reverse primers may be removed by the same or different restriction endonucleases. Any type of restriction endonuclease may be used to remove the primers/primer binding sites from nucleic acid sequences. A wide variety of restriction endonucleases having specific binding and/or cleavage sites are commercially available, for example, from New England Biolabs (Beverly, Mass.). In various embodiments, restriction endonucleases that produce 3' overhangs, 5' overhangs or blunt ends may be used. When using a restriction endonuclease that produces an overhang, an exonuclease (e.g., RecJ$_f$, Exonuclease I, Exonuclease T, S$_1$ nuclease, P$_1$ nuclease, mung bean nuclease, T4 DNA polymerase, CEL I nuclease, etc.) may be used to produce blunt ends. Alternatively, the sticky ends formed by the specific restriction endonuclease may be used to facilitate assembly of subassemblies in a desired arrangement. In an exemplary embodiment, a primer/primer binding site that contains a binding and/or cleavage site for a type IIs restriction endonuclease may be used to remove the temporary primer.

The term "type-IIs restriction endonuclease" refers to a restriction endonuclease having a non-palindromic recognition sequence and a cleavage site that occurs outside of the recognition site (e.g., from 0 to about 20 nucleotides distal to the recognition site). Type IIs restriction endonucleases may create a nick in a double stranded nucleic acid molecule or may create a double stranded break that produces either blunt or sticky ends (e.g., either 5' or 3' overhangs). Examples of Type IIs endonucleases include, for example, enzymes that produce a 3' overhang, such as, for example, Bsr I, Bsm I, BstF5 I, BsrD I, Bts I, Mnl I, BciV I, Hph I, Mbo II, Eci I, Acu I, Bpm I, Mme I, BsaX I, Bcg I, Bae I, Bfi I, TspDT I, TspGW I, Taq II, Eco57 I, Eco57M I, Gsu I, Ppi I, and Psr I; enzymes that produce a 5' overhang such as, for example, BsmA I, Ple I, Fau I, Sap I, BspM I, SfaN I, Hga I, Bvb I, Fok I, BceA I, BsmF I, Ksp632 I, Eco31 I, Esp3 I, Aar I; and enzymes that produce a blunt end, such as, for example, Mly I and Btr I. Type-IIs endonucleases are commercially available and are well known in the art (New England Biolabs, Beverly, Mass.).

Some embodiments of the devices and methods provided herein use oligonucleotides that are immobilized on a solid support. A solid support refers to a porous or non-porous solvent insoluble material. As used herein "porous" means that the material contains pores having substantially uniform diameters (for example in the nm range). Porous materials include paper, synthetic filters etc. In such porous materials, the reaction may take place within the pores. The support can have any one of a number of shapes, such as pin, strip, plate, disk, rod, cylindrical structure, particle, including bead, and the like. The support can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly (4-methylbutene), polystyrene, polymethacrylate, poly(ethylene terephthalate), nylon, poly(vinyl butyrate), polyvinylidene difluoride (PVDF) membrane, glass, controlled pore glass, magnetic controlled pore glass, ceramics, metals, and the like etc.; either used by themselves or in conjunction with other materials.

In some embodiments, oligonucleotides are synthesized on an array format. For example, single stranded oligonucleotides are synthesized in situ on a common support wherein each oligonucleotide is synthesized on a separate feature (or spot) on the substrate. It should be appreciated that each oligonucleotide fragment can be of any length, but is typically 10-400 bases long. Arrays may be constructed, custom ordered or purchased from a commercial vendor (e.g., Agilent, Affymetrix, Nimblegen). Various methods of construction are well known in the art e.g. maskless array synthesizers, light directed methods utilizing masks, flow channel methods, spotting methods etc.

In some embodiments, construction and/or selection oligonucleotides may be synthesized on a solid support using maskless array synthesizer (MAS). Maskless array synthesizers are described, for example, in PCT application No. WO 99/42813 and in corresponding U.S. Pat. No. 6,375,903. Other examples are known of maskless instruments which can fabricate a custom DNA microarray in which each of the features in the array has a single stranded DNA molecule of desired sequence.

Other methods for synthesizing construction and/or selection oligonucleotides include, for example, light-directed methods utilizing masks, flow channel methods, spotting methods, pin-based methods, and methods utilizing multiple supports.

Light directed methods utilizing masks (e.g., VLSIPS™ methods) for the synthesis of oligonucleotides is described, for example, in U.S. Pat. Nos. 5,143,854, 5,510,270 and 5,527,681. These methods involve activating predefined regions of a solid support and then contacting the support with a preselected monomer solution. Selected regions can be activated by irradiation with a light source through a mask much in the manner of photolithography techniques used in integrated circuit fabrication. Other regions of the support remain inactive because illumination is blocked by the mask and they remain chemically protected. Thus, a light pattern defines which regions of the support react with a given monomer. By repeatedly activating different sets of predefined regions and contacting different monomer solutions with the support, a diverse array of polymers is produced on the support. Other steps, such as washing unreacted monomer solution from the support, can be optionally used. Other applicable methods include mechanical techniques such as those described in U.S. Pat. No. 5,384,261.

Additional methods applicable to synthesis of construction and/or selection oligonucleotides on a single support are described, for example, in U.S. Pat. No. 5,384,261. For example, reagents may be delivered to the support by either (1) flowing within a channel defined on predefined regions or (2) "spotting" on predefined regions. Other approaches, as well as combinations of spotting and flowing, may be employed as well. In each instance, certain activated regions of the support are mechanically separated from other regions when the monomer solutions are delivered to the various reaction sites. Flow channel methods involve, for example, microfluidic systems to control synthesis of oligonucleotides on a solid support. For example, diverse polymer sequences may be synthesized at selected regions of a solid support by forming flow channels on a surface of the support through which appropriate reagents flow or in which appropriate reagents are placed. Spotting methods for preparation of oligonucleotides on a solid support involve delivering reactants in relatively small quantities by directly depositing them in selected regions. In some steps, the entire support surface can be sprayed or otherwise coated with a solution, if it is more efficient to do so. Precisely measured aliquots of monomer solutions may be deposited dropwise by a dispenser that moves from region to region.

Pin-based methods for synthesis of oligonucleotides on a solid support are described, for example, in U.S. Pat. No. 5,288,514. Pin-based methods utilize a support having a plurality of pins or other extensions. The pins are each inserted simultaneously into individual reagent containers in a tray. An array of 96 pins is commonly utilized with a 96-container tray, such as a 96-well microtitre dish. Each tray is filled with a particular reagent for coupling in a particular chemical reaction on an individual pin. Accordingly, the trays will often contain different reagents. Since the chemical reactions have been optimized such that each of the reactions can be performed under a relatively similar set of reaction conditions, it becomes possible to conduct multiple chemical coupling steps simultaneously.

In yet another embodiment, a plurality of construction and/or selection oligonucleotides may be synthesized on multiple supports. On example is a bead based synthesis method which is described, for example, in U.S. Pat. Nos. 5,770,358; 5,639,603; and 5,541,061. For the synthesis of molecules such as oligonucleotides on beads, a large plurality of beads is suspended in a suitable carrier (such as water) in a container. The beads are provided with optional spacer molecules having an active site to which is complexed, optionally, a protecting group. At each step of the synthesis, the beads are divided for coupling into a plurality of containers. After the nascent oligonucleotide chains are deprotected, a different monomer solution is added to each container, so that on all beads in a given container, the same nucleotide addition reaction occurs. The beads are then washed of excess reagents, pooled in a single container, mixed and re-distributed into another plurality of containers in preparation for the next round of synthesis. It should be noted that by virtue of the large number of beads utilized at the outset, there will similarly be a large number of beads randomly dispersed in the container, each having a unique oligonucleotide sequence synthesized on a surface thereof after numerous rounds of randomized addition of bases. An individual bead may be tagged with a sequence which is unique to the double-stranded oligonucleotide thereon, to allow for identification during use.

Pre-synthesized oligonucleotide and/or polynucleotide sequences may be attached to a support or synthesized in situ using light-directed methods, flow channel and spotting methods, inkjet methods, pin-based methods and bead-based methods set forth in the following references: McGall et al. (1996) Proc. Natl. Acad. Sci. U.S.A. 93:13555; Synthetic DNA Arrays In Genetic Engineering, Vol. 20:111, Plenum Press (1998); Duggan et al. (1999) Nat. Genet. S21:10; Microarrays: Making Them and Using Them In Microarray Bioinformatics, Cambridge University Press, 2003; U.S. Patent Application Publication Nos. 2003/0068633 and 2002/0081582; U.S. Pat. Nos. 6,833,450, 6,830,890, 6,824,866, 6,800,439, 6,375,903 and 5,700,637; and PCT Publication Nos. WO 04/031399, WO 04/031351, WO 04/029586, WO 03/100012, WO 03/066212, WO 03/065038, WO 03/064699, WO 03/064027, WO 03/064026, WO 03/046223, WO 03/040410 and WO 02/24597; incorporated herein by reference in their entirety for all purposes. In a preferred embodiment, pre-synthesized are attached to a support or are synthesized using a spotting methodology wherein monomers solutions are deposited dropwise by a dispenser that move from region to region (e.g. ink jet). In some embodiments, oligonucleotides are spotted on a solid support using, for example, a mechanical wave actuated dispenser.

In some embodiments of the technology provided herein, polynucleotides are assembled by multiplex nucleic acid assembly. Multiplex nucleic acid assembly relates to the assembly of a plurality of oligonucleotides and/or polynucleotides to generate a longer nucleic acid product. The polynucleotide product may be at least about 1, 2, 3, 4, 5, 8, 10, 15, 20, 25, 30, 40, 50, 75, or 100 kilobases (kb), or 1 megabase (mb), or longer. In some embodiments, oligonucleotides or polynucleotides are assembled via a hierarchical and sequential approach. Oligonucleotides or polynucleotides to be assembled are synthesized or spotted on adjacent features or spots on the support. For example, two oligonucleotides having complementary regions may be immobilized or synthesized in close proximity to each other. Spot or features or location may be placed every 5 µm, 10 µm, 25 µm, 50 µm, 75 µm or above. However smaller or larger spacing may be used. In some embodiments, the solid support has 1000 to $10^6$ features or active sites.

It should be appreciated that the description of the assembly reactions of oligonucleotides that are supported on adjacent features on the support is not intended to be limiting. For example, additional different synthetic oligonucleotides or polynucleotides (e.g. single stranded or double stranded oligonucleotides) may be included in an assembly reaction together with solid-supported oligonucleotides in order to generate a polynucleotide of interest. The additional synthetic oligonucleotide can be prepared by conventional phosphoramidite chemistry. Phosphoramidite chemistry can be carried out using commercially available machines as is available, for example, from Integrated DNA Technologies.

In some embodiments, reagents are spotted or jetted onto the solid support. Droplets containing enzymes, dNTP, buffer, primers or any combination thereof are spotted to match the DNA spots on the microarray. In other embodiments, the solution deposited on the solid support comprises one or more different and unique oligonucleotide molecules.

In various embodiments, a mechanical wave actuated dispenser can be used for transferring small volumes of fluids (e.g., nanoliter, picoliter, or sub-picoliter). A mechanical wave actuated dispenser can be a piezoelectric inkjet device or an acoustic liquid handler. A piezoelectric inkjet device can eject fluids by actuating a piezoelectric actuation mechanism, which forces fluid droplets to be ejected. Piezoelectrics in general have good operating bandwidth and can generate large forces in a compact size. Some of the commercially available piezoelectric inkjet microarraying instruments include those from Perkin Elmer (Wellesley, Mass.), GeSim (Germany) and MicroFab (Plano, Tex.). Typical piezoelectric dispensers can create droplets in the picoliter range and with coefficient of variations of 3-7%. Inkjetting technologies and devices for ejecting a plurality of fluid droplets toward discrete sites on a substrate surface for deposition thereon have been described in a number of patents such as U.S. Pat. Nos. 6,511,849; 6,514,704; 6,042,211; 5,658,802, the disclosure of which are incorporated herein by reference.

In one embodiment, the fluid or solution deposition is performed using an acoustic liquid handler or ejector. Acoustic devices are non-contact dispensing devices able to dispense small volume of fluid (e.g. picoliter to microliter), see for example Echo 550 from Labcyte (CA), HTS-01 from EDC Biosystems. Acoustic technologies and devices for acoustically ejecting a plurality of fluid droplets toward discrete sites on a substrate surface for deposition thereon have been described in a number of patents such as U.S. Pat. Nos. 6,416,164; 6,596,239; 6,802,593; 6,932,097; 7,090,333 and US Patent Application 2002-0037579, the disclosure of which are incorporated herein by reference. The acoustic device includes an acoustic radiation generator or transducer that may be used to eject fluid droplets from a reservoir (e.g. microplate wells) through a coupling medium. The pressure of the focused acoustic waves at the fluid surface creates an upwelling, thereby causing the liquid to urge upwards so as to eject a droplet, for example from a well of a source plate, to a receiving plate positioned above the fluid reservoir. The volume of the droplet ejected can be determined by selecting the appropriate sound wave frequency. Methods and devices provided herein preferably involve small assembly reaction volumes or microvolumes. One should appreciate that the shape of small volumes of liquids is governed and maintained by the surface tension of the liquid. In some embodiments, the microvolume is bounded completely or almost completely by free surface forming a droplet or microdrop. In a preferred embodiment, the assembly reaction microvolume may be in the form of a droplet. In some embodiments, reaction microvolumes of between about 0.5 pL and about 100 nL may be used. However, smaller or larger volumes may be used. In some embodiments, a mechanical wave actuated dispenser may be used for transferring volumes of less than 100 nL, less than 10 nL, less than 5 nL, less than 100 pL, less than 10 pL, or about 0.5 pL or less. In some embodiments, the mechanical wave actuated dispenser can be a piezoelectric inkjet device or an acoustic liquid handler.

Figure 1B:
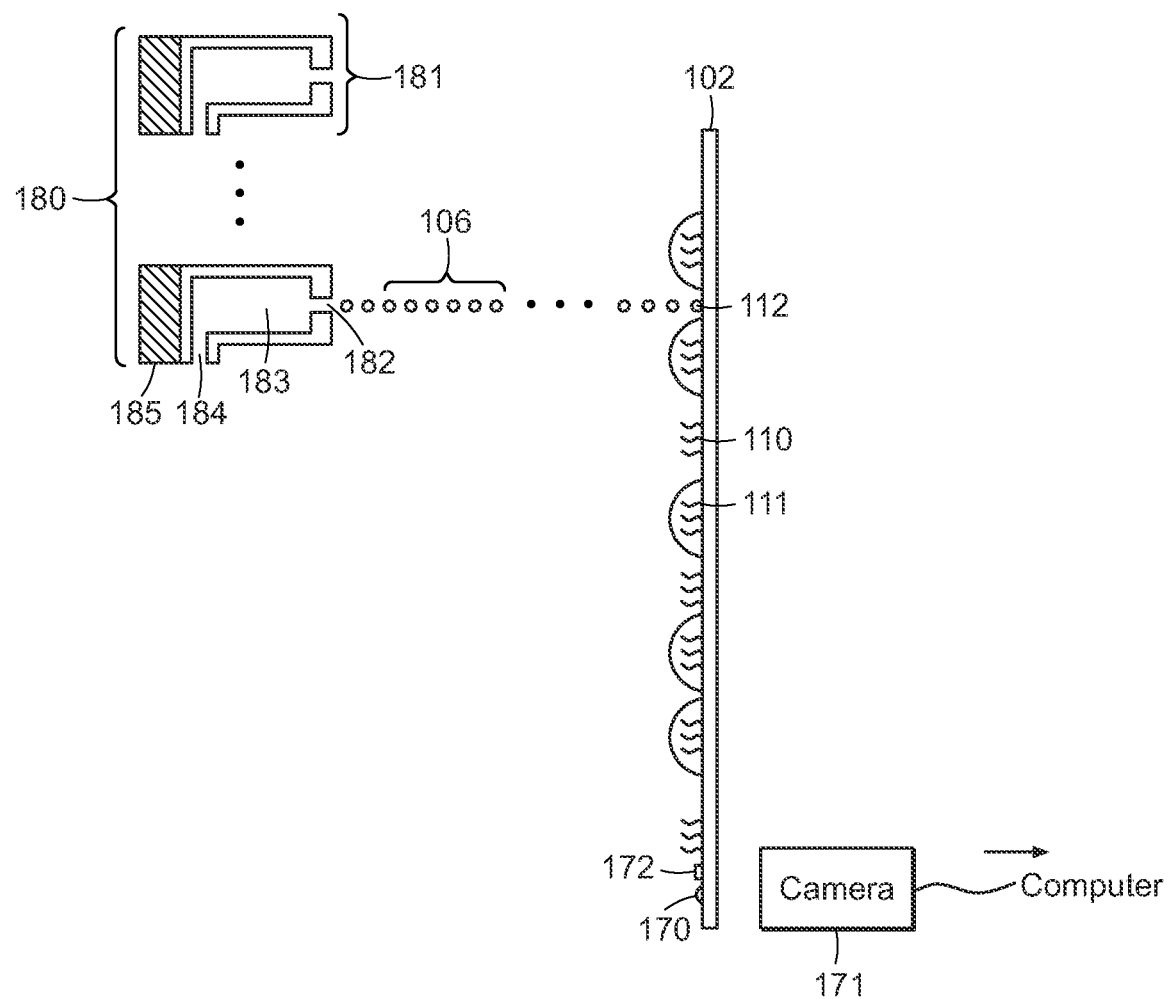
FIG. 1B illustrates an embodiment using an inkjet device for droplet dispensing. The head assembly (180) includes multiple jetting modules (181), with each module containing at least one reservoir (183) having at least one inlet (184). Each jetting module can have one or more than one nozzle (182), which can be arranged in an 1D or 2D array to form a nozzle pattern. The nozzles can have well defined dimensions to allow droplets (106) to form under the influence of a mechanical wave generated by a transducer (185). Each nozzle in a jetting module can be controlled by an independent transducer. Alternatively, multiple nozzles can be controlled by a common transducer. The head assembly can have one, or two, or three degrees of freedom to move in physical space. The transducers can be controlled, for example, by electronics that are in communication with a computer.

In some embodiments, the source plate comprising primers, master mix, release chemicals, enzymes, or any combination thereof and the destination plates comprising the oligonucleotides or polynucleotides are matched up to allow proper delivery or spotting of the reagent to the proper site. The mechanical wave actuated dispenser may be coupled with a microscope and/or a camera to provide positional selection of deposited spots. A camera may be placed on both sides of the destination plate or substrate. A camera may be used to register to the positioning on the array especially if the DNA is coupled with a fluorescent label. As shown in FIG. 1A and described below components of the device include: 101: Source well plate; containing the reagents for reactions, this element can travel in at least 2 degree-of-freedom (>2DOF); 102: Solid support, with solid attached molecules, this element can travel in at least 2 degree-of-freedom (>2DOF); 103: Transducer, to create a mechanical wave which causes droplets to form and travel, this element can travel in at least 2 degree-of-freedom (>2DOF); 104: Coupling fluid, to allow the mechanical wave to couple to the well plate (101); 105: Reagents inside a well on the source well plate (101); 171: A camera (such as an electronic camera) used to provide physical registration (positioning) and 172: A surface mark fixed on the solid support (102) to provide a reference position on the solid support. FIG. 1B shows another example where an inkjet device 180 (e.g., piezoelectric) can be used to dispense droplets.

A mechanical wave actuated dispenser (103, 180) can be used to create traveling droplets (106) from a reagent source (101). The created traveling droplets (106) can be deposited onto a receiving surface, in this case a solid support (102). The position of the deposited droplets (111) on the solid support (102) can be controlled by the relative position of 101 and 102. Furthermore, there can be an existing pattern of molecules (110) on the solid support (102). The traveling droplets (106) can be aligned to the existing pattern on the surface. One should appreciate that the alignment and the dispensing are crucial steps in some embodiments. Multiple reagents can be dispensed to the sites on the surface in a sequential process. The solid support (102) is also known as the destination surface. This surface may have molecules that are previously deposited on the surface. These molecules can represent a complex pattern on the surface of (102). Furthermore, these molecules may be covalently bonded, hydrogen bonded, or not bonded (just deposited in solution or dry form) to the surface of (102). In a preferred embodiment, the droplets (106) created by the mechanical wave actuated dispenser (103, 180) are aimed and deposited at desired positions on the surface of 102. Adjacent surface droplets (111) can be combined by the creation of "merger" droplets (112) by positioning the merger droplets (112) in between or around the surface droplets (111). In this embodiment, the alignment of the droplets (106) to the solid support (102) and the molecules attached to the solid support (110) is crucial. A system can be devised to align the droplet to the patterns (molecules) on 102 by using a variety of sensing methods. In some embodiments, the position of the dispensed droplet in relation to the existing pattern on 102 is known or determinable by the user. The detection method can be based on acoustics, electrical conductive, electrical capacitive, or optical.

In FIG. 1A, the alignment is illustrated using an optical setup. A set of test droplets (170) can be dispensed to several locations on the solid support (102). The relative position between the test droplets (170: A surface droplet dispensed for the purpose of alignment of the droplet to the solid attached molecules (111)) and fixed registration marks (172: A surface mark fixed on the solid support (102) to provide a reference position on the solid support) on the surface of 102 can provide information on the alignment between the source plate (101) and the destination surface (102). A computer system can be used to calculate a set of correction (offset) parameters, which will be used to correct the alignment by adjusting the positioning motors controlling the position of 101, 102, and 103.

The same mechanical wave actuated dispenser can be used to dispense miscible or non-miscible solution onto the droplet. Miscible solution (e.g. in water) may contain enzymes, dNTP, buffer, primers or any combination thereof. One should appreciate that the size of the droplet is determined by the volume and by the surface tension of the solution. One drawback is that the smaller the droplet, the faster it will evaporate. In some embodiments, a non-miscible solution (e.g. oil) can be used. A non-miscible solution will have the advantage to protect the droplet from evaporation and from its environment.

Methods for assembling large polynucleotides using oligonucleotides attached to a solid support are provided herein. In one embodiment, droplets containing polymerase, dNTPs, buffer, chemicals, primers or any combination thereof are spotted or jetted onto specific features or location containing oligonucleotides (or spots) on the solid support. In some embodiments, the solid surface does not any free hydroxyl group. One should appreciate that in some embodiments that the features or active or synthesis surface are hydrophilic and the non-active or inert surface areas (e.g. between features) are hydrophobic. According to some embodiments, a protective coating such as a hydrophilic or hydrophobic coating (depending upon the nature of the solvent) is utilized over portions of the substrate to be protected, sometimes in combination with materials that facilitate wetting by the reactant solution in other regions. In some embodiments, portion of the solid support comprises hydrophilic sites and portion of the solid support comprises hydrophobic sites. In some embodiments, a hydrophilic site is inert to conditions of in situ synthesis and assembly. Yet in other embodiments, a hydrophobic site is inert to conditions of in situ synthesis and assembly. A hydrophilic site may include free amino, hydroxyl, carboxyl, thiol, amido, halo or sulfonate group as well as modified forms thereof. A hydrophobic site may include alkyl, fluoro group as well as modified forms thereof. The synthesis sites may support covalent or non-covalent attachment of chemicals or biological molecules. For instance, the hydrophilic sites may support attachment of a linker moiety (polylysine etc.). In some embodiments, the synthesis surface area is located at the extremity of the solid support. For example, the solid support may be first reacted with a suitable reagent to form a hydrophilic surface. Part of the solid support is then treated with a suitable reagent to form hydrophobic surface to allow polymer synthesis. Alternatively, the solid support may be first reacted with suitable reagent to form a hydrophilic surface. Part of the hydrophilic surface may be protected with a suitable reagent to form a hydrophobic surface. The hydrophilic synthesis surface area may then be deprotected to allow polymer synthesis. Alternatively, the area between hydrophilic synthesis surfaces may be coated with a dewetting agent such as wax or polymers. The dewetting agent may be inkjetted or patterned with other techniques (e.g. lithography). One should appreciate that after dispensing the droplets onto the active sites, droplets are separated from the others by surface tension of the solution. In some embodiments, merging or mixing of two adjacent droplets is prevented by the hydrophobic area around the active sites. In another embodiment, a dewetting agent is inkjetted or spotted in between the active features to build a vertical height between the active features thereby forming a micro-well array. For example, wax or polymers can be spotted using a mechanical wave actuated dispenser.

In some embodiments, oligonucleotides or polynucleotides are amplified within the droplet by solid phase PCR thereby eluting the amplified sequences into the droplet. In other embodiments, oligonucleotides or polynucleotides are first detached form the solid support and than amplified. In one embodiment, covalently-attached oligonucleotides are translated into surface supported DNA molecules through a process of gaseous cleavage using amine gas. Oligonucleotides can be cleaved with ammonia, or other amines, in the gas phase whereby the reagent gas comes into contact with the oligonucleotide while attached to, or in proximity to, the solid support (see Boal et al., NAR, 1996 (24(15):3115-7), U.S. Pat. Nos. 5,514,789; 5,738,829 and 6,664,388). In this process, the covalent bond attaching the oligonucleotides to the solid support is cleaved by exposing the solid support to the amine gas under elevated pressure and/or temperature.

In some embodiments, oligonucleotides or polynucleotides are extended once to prepare a complementary strand hybridized to the surface-bound template. A second processing step is performed to melt and remove the amplicons from the templates. This second processing step can be achieved via enzymatic activity (e.g., helicase), buffer condition, temperature, or other methods where hydrogen bonds between complementary strands could be compromised. The extension followed by melting process can be performed repeatedly to achieve multiple copies of each template.

In some embodiments, oligonucleotides are synthesized in situ and comprises a cleavable linker moiety. Oligonucleotides may then be cleaved by exposure to conditions such as acid, base, oxidation, reduction, heat, light, metal ion catalysis, displacement or elimination chemistry or by enzymatic cleavage. Under such conditions, oligonucleotides can be eluted within the droplet without being amplified.

In one embodiment, oligonucleotides may be attached to a solid support through a cleavable linkage moiety. For example, the solid support may be functionalized to provide cleavable linkers for covalent attachment to the oligonucleotides. The linker moiety may be of six or more atoms in length. Alternatively, the cleavable moiety may be within an oligonucleotide and may be introduced during in situ synthesis. A broad variety of cleavable moieties are available in the art of solid phase and microarray oligonucleotide synthesis (see e.g., Pon, R., Methods Mol. Biol. 20:465-496 (1993); Verma et al., Annu. Rev. Biochem. 67:99-134 (1998); U.S. Pat. Nos. 5,739,386, 5,700,642 and 5,830,655; and U.S. Patent Publication Nos. 2003/0186226 and 2004/0106728). A suitable cleavable moiety may be selected to be compatible with the nature of the protecting group of the nucleoside bases, the choice of solid support, and/or the mode of reagent delivery, among others. In an exemplary embodiment, the oligonucleotides cleaved from the solid support contain a free 3'-OH end. Alternatively, the free 3'-OH end may also be obtained by chemical or enzymatic treatment, following the cleavage of oligonucleotides. The cleavable moiety may be removed under conditions which do not degrade the oligonucleotides. Preferably the linker may be cleaved using two approaches, either (a) simultaneously under the same conditions as the deprotection step or (b) subsequently utilizing a different condition or reagent for linker cleavage after the completion of the deprotection step.

The covalent immobilization site may either be at the 5' end of the oligonucleotide or at the 3' end of the oligonucleotide. In some instances, the immobilization site may be within the oligonucleotide (i.e. at a site other than the 5' or 3' end of the oligonucleotide). The cleavable site may be located along the oligonucleotide backbone, for example, a modified 3'-5' internucleotide linkage in place of one of the phosphodiester groups, such as ribose, dialkoxysilane, phosphorothioate, and phosphoramidate internucleotide linkage. The cleavable oligonucleotide analogs may also include a substituent on, or replacement of, one of the bases or sugars, such as 7-deazaguanosine, 5-methylcytosine, inosine, uridine, and the like.

In one embodiment, cleavable sites contained within the modified oligonucleotide may include chemically cleavable groups, such as dialkoxysilane, 3'-(S)-phosphorothioate, 5'-(S)-phosphorothioate, 3'-(N)-phosphoramidate, 5'-(N)phosphoramidate, and ribose. Synthesis and cleavage conditions of chemically cleavable oligonucleotides are described in U.S. Pat. Nos. 5,700,642 and 5,830,655. For example, depending upon the choice of cleavable site to be introduced, either a functionalized nucleoside or a modified nucleoside dimer may be first prepared, and then selectively introduced into a growing oligonucleotide fragment during the course of oligonucleotide synthesis. Selective cleavage of the dialkoxysilane may be effected by treatment with fluoride ion. Phosphorothioate internucleotide linkage may be selectively cleaved under mild oxidative conditions. Selective cleavage of the phosphoramidate bond may be carried out under mild acid conditions, such as 80% acetic acid. Selective cleavage of ribose may be carried out by treatment with dilute ammonium hydroxide.

In another embodiment, a non-cleavable hydroxyl linker may be converted into a cleavable linker by coupling a special phosphoramidite to the hydroxyl group prior to the phosphoramidite or H-phosphonate oligonucleotide synthesis as described in U.S. Patent Application Publication No. 2003/0186226. The cleavage of the chemical phosphorylation agent at the completion of the oligonucleotide synthesis yields an oligonucleotide bearing a phosphate group at the 3' end. The 3'-phosphate end may be converted to a 3' hydroxyl end by a treatment with a chemical or an enzyme, such as alkaline phosphatase, which is routinely carried out by those skilled in the art.

In another embodiment, the cleavable linking moiety may be a TOPS (two oligonucleotides per synthesis) linker (see e.g., PCT publication WO 93/20092). For example, the TOPS phosphoramidite may be used to convert a non-cleavable hydroxyl group on the solid support to a cleavable linker. A preferred embodiment of TOPS reagents is the Universal TOP S™ phosphoramidite. Conditions for Universal TOPS™ phosphoramidite preparation, coupling and cleavage are detailed, for example, in Hardy et al, Nucleic Acids Research 22(15):2998-3004 (1994). The Universal TOPS™ phosphoramidite yields a cyclic 3' phosphate that may be removed under basic conditions, such as the extended ammonia and/or ammonia/methylamine treatment, resulting in the natural 3' hydroxy oligonucleotide.

In another embodiment, a cleavable linking moiety may be an amino linker. The resulting oligonucleotides bound to the linker via a phosphoramidite linkage may be cleaved with 80% acetic acid yielding a 3'-phosphorylated oligonucleotide.

In another embodiment, the cleavable linking moiety may be a photocleavable linker, such as an ortho-nitrobenzyl photocleavable linker. Synthesis and cleavage conditions of photolabile oligonucleotides on solid supports are described, for example, in Venkatesan et al. J. of Org. Chem. 61:525-529 (1996), Kahl et al., J. of Org. Chem. 64:507-510 (1999), Kahl et al., J. of Org. Chem. 63:4870-4871 (1998), Greenberg et al., J. of Org. Chem. 59:746-753 (1994), Holmes et al., J. of Org. Chem. 62:2370-2380 (1997), and U.S. Pat. No. 5,739,386. Ortho-nitrobenzyl-based linkers, such as hydroxymethyl, hydroxyethyl, and Fmoc-aminoethyl carboxylic acid linkers, may also be obtained commercially.

Figure 2:
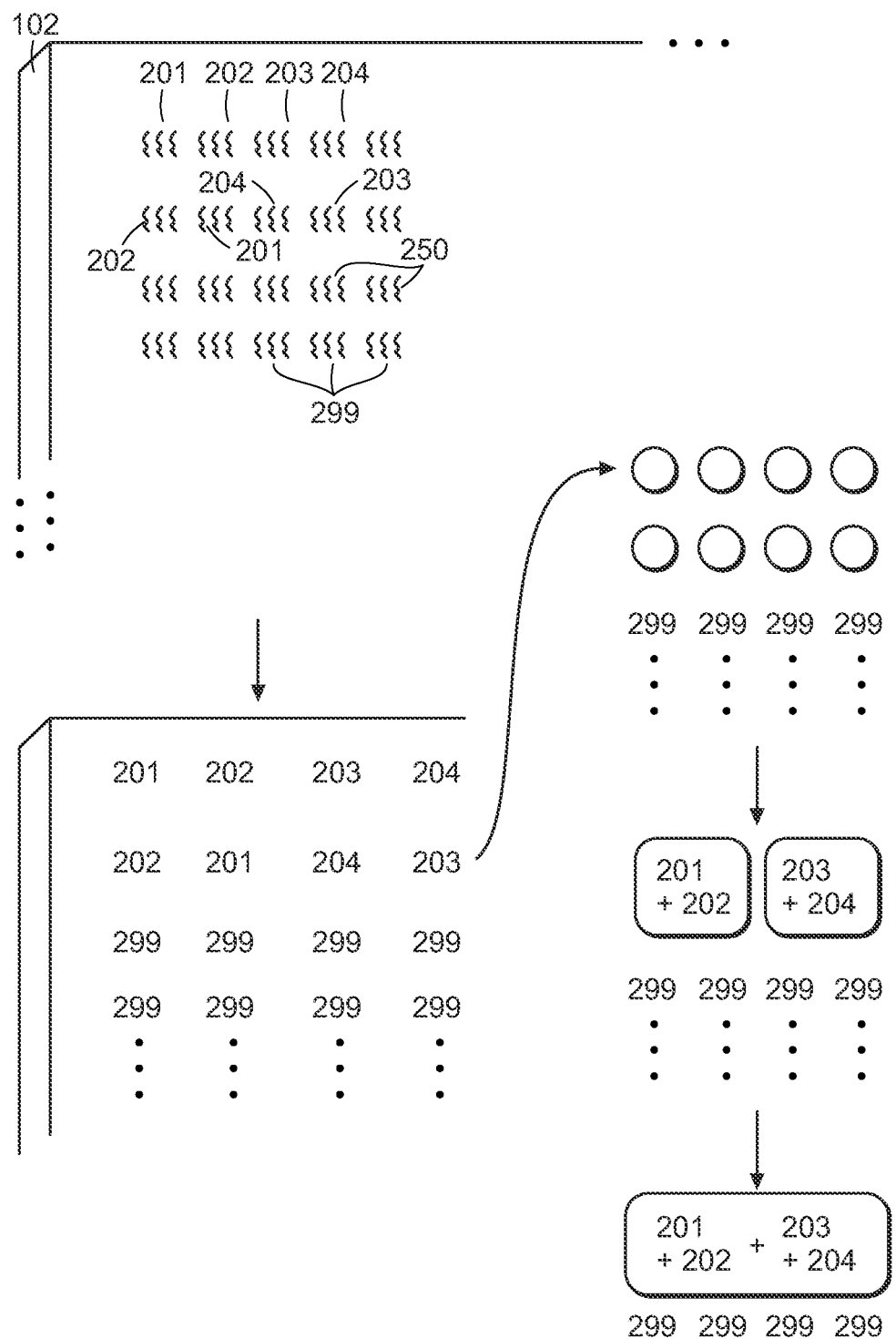
FIG. 2 illustrates an embodiment of a solid support comprising different and unique molecules (201, 202, 203, 204) supported or attached to the surface of 102, a unique molecule (250) supported or attached to the surface of 102 at multiple positions other unique molecules (299) supported or attached to the surface of 102.
Figure 3A:
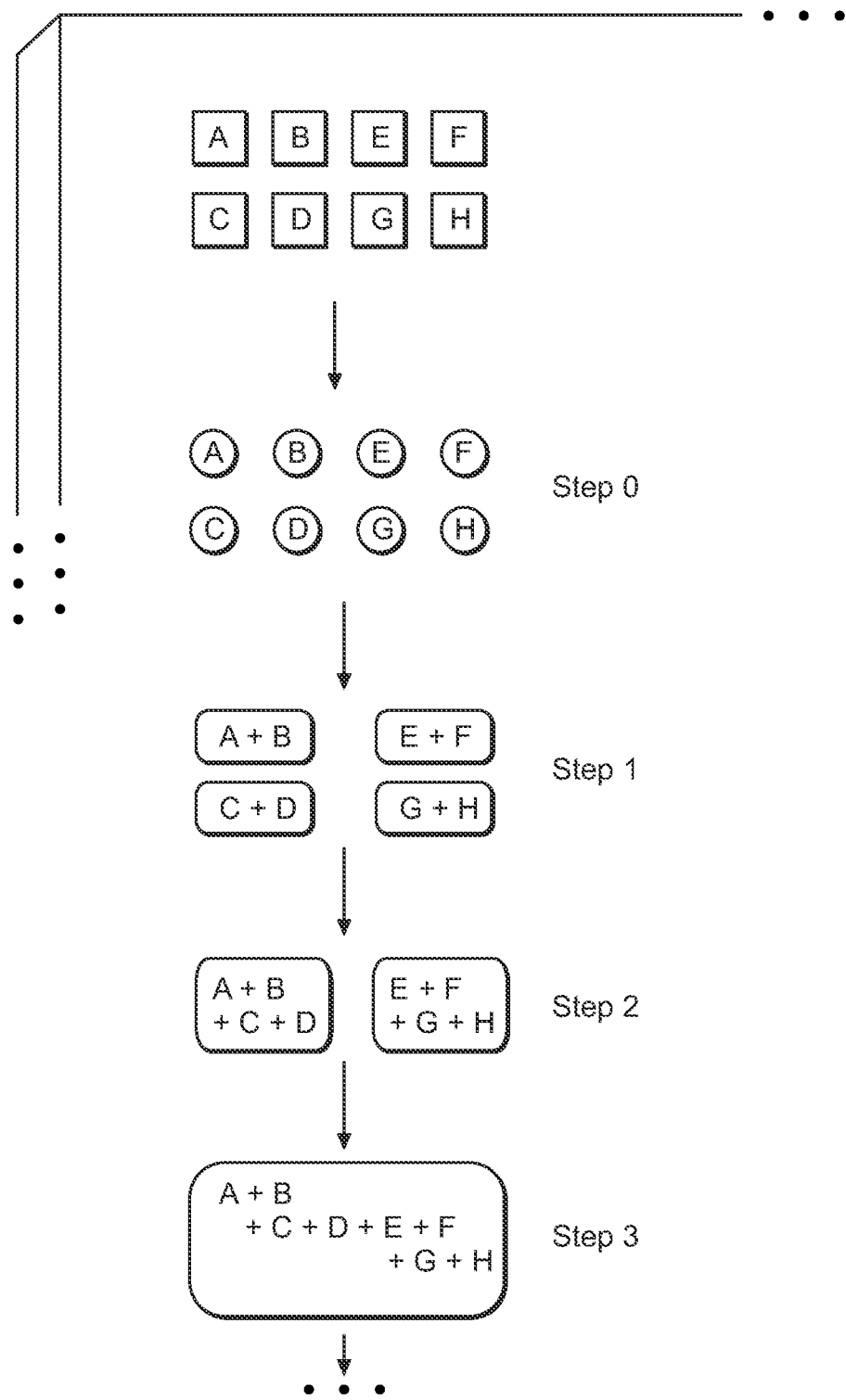
FIG. 3A illustrates an embodiment of a solid support comprising different molecules (A, B, C, etc.) and a non-limiting example of an assembly strategy.
Figure 3B:
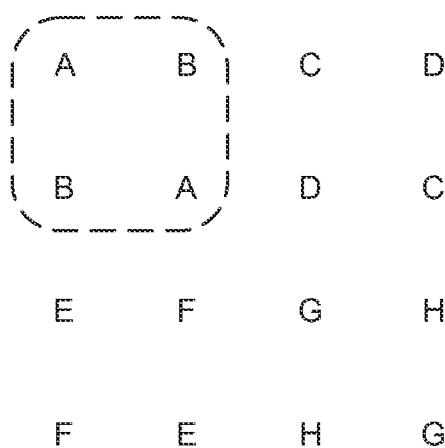
FIG. 3B illustrates a non-limiting example of an assembly strategy.
Figure 3C:
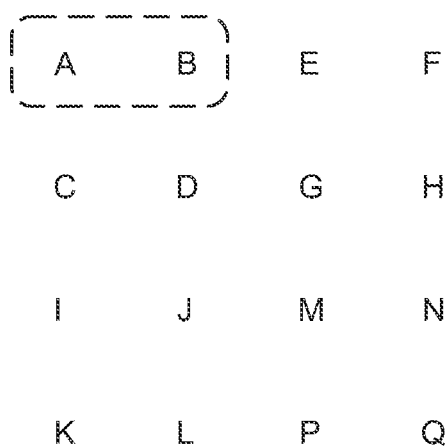
FIG. 3C illustrates a non limiting example of a hierarchical assembly strategy.

In some embodiments, two adjacent droplets containing two multiple copies of different oligonucleotides or polynucleotides in solution are combined by merging the appropriate droplets on the solid support as illustrated in FIG. 2 and FIGS. 3A-3D. In FIG. 2, the solid support comprises different and unique molecules (201, 202, 203, 204) supported or attached to the surface of 102, a unique molecule (250) supported or attached to the surface of 102 at multiple positions other unique molecules (299) supported or attached to the surface of 102. On the solid support surface (102) an existing pattern of molecules can be found. Different molecules or oligonucleotides can exist at different positions, as shown by the placement of 201, 202, 203, 204, 250, and 299. One should appreciate that the arrangement of these unique molecules (201, 202, 203, 204) can be designed to strategically allow the subsequent combining of the contents of these sites. For example, these unique molecules can be arranged in a checker board pattern. The first checker board pattern contains 201 and 202. After individual reactions within the microvolume of 201 and 202 are complete, the user can choose to combine the content of 201 and 202 by forming a droplet that encompasses both 201 and 202 sites. In another subsequent step, the content of 201+202 can be combined with the content of 203+204, to form a reaction that contains all four reaction products of the unique molecules (201, 202, 203, 204). FIG. 3A illustrates the same general concept with A, B, C, D. In step 0, all the unique molecules are reacted in separate volumes. In Step 1, the adjacent sites are combined, to give A+B, and C+D, etc. In Step 2, A+B can be combined with C+D, and etc. In Step 3, another level of aggregation is added. One should appreciate that there is no limit to the number of steps that can be implemented. In FIG. 3B and FIG. 3C, two possible arrangement strategies are outlined. In the first strategy, some adjacent sites comprise the same molecules or oligonucleotides (e.g. A and B) and the four sites may be combined to generate a circular droplet (FIG. 3B). In the second strategy, each site comprises a unique and different molecule or oligonucleotide (FIG. 3C).

For example, with reference to FIG. 2, solid supported oligonucleotide 201 and oligonucleotides 202 may be amplified in first stage droplet 1 and first stage droplet 2. After amplification, each first stage droplet contains one amplified double stranded oligonucleotide sequence. In embodiments, multiple copies of oligonucleotides 201 and multiple copies of oligonucleotide 202 are eluted within the first stage droplet 1 and the first stage droplet 2, respectively. The two first stage droplets being in close proximity to each other are combined to form a second stage droplet. In some embodiments, two different or more oligonucleotides or polynucleotides may be immobilized or synthesized at the same location (or feature) on the solid support thereby facilitating their interaction after amplification within the same droplet. See e.g. US 2004/0101894. In some embodiments, droplets are merged to form bigger droplets by adding, or spotting additional "merger" droplets in between or around the appropriate original droplets. The additional "merger" droplets may contain enzyme (e.g. polymerase, ligase, etc.), additional oligonucleotides and all reagents to allow assembly by PCR or by ligation (enzymatic or chemical) or by any combination of enzymatic reaction. For example, oligonucleotides in a given droplet may hybridize to each other and may assemble by PCR or ligation. The bigger droplets or second stage droplets contain polynucleotides subassemblies and can be subsequently merged to form larger droplets or third stage droplet containing larger fragments. As used herein the term subassembly refers to a nucleic acid molecule that has been assembled from a set of oligonucleotides. Preferably, a subassembly is at least 2-fold or more long than the oligonucleotides. For example, a subassembly may be about 100, 200, 300, 400, 500, 600, or ore bases long. One should appreciate that the use of droplets as isolated reaction volume enables a highly parallel system. In some embodiments, at least 100, at least 1,000 reactions can take place in parallel. In some embodiments, the primers are immobilized on the substrate in close proximity to the spots containing the oligonucleotides to be assembled. In some embodiments, the primers are cleaved in situ. In some embodiments, the primers are supported on the solid support. The primers may then be cleaved in situ and eluted within a droplet that will subsequently merged with a droplet containing solid supported or eluted oligonucleotides.

In some embodiments, mechanical wave actuated delivery techniques (e.g., a surface acoustic wave device, a piezoelectric device, or other force transducer) can be used to transfer droplets from a first spot or position to a second spot or position on a solid support, forming hopping droplets. A hopping droplet can include one or more oligonucleotides, enzymes, buffers, dNTPs, etc. One or more of denaturing, restriction, annealing, ligation, and chain extension can be carried out in the hopping droplet. The first and second spots can be two neighboring spots on a solid support or separated by any distance. The two spots can each have a feature. In one embodiment, the features at the two spots share the same or complementary sequence at one terminus. The hopping droplet technique can be combined with traveling droplet for the assembly of a target nucleic acid product or intermediate.

Figure 3D:
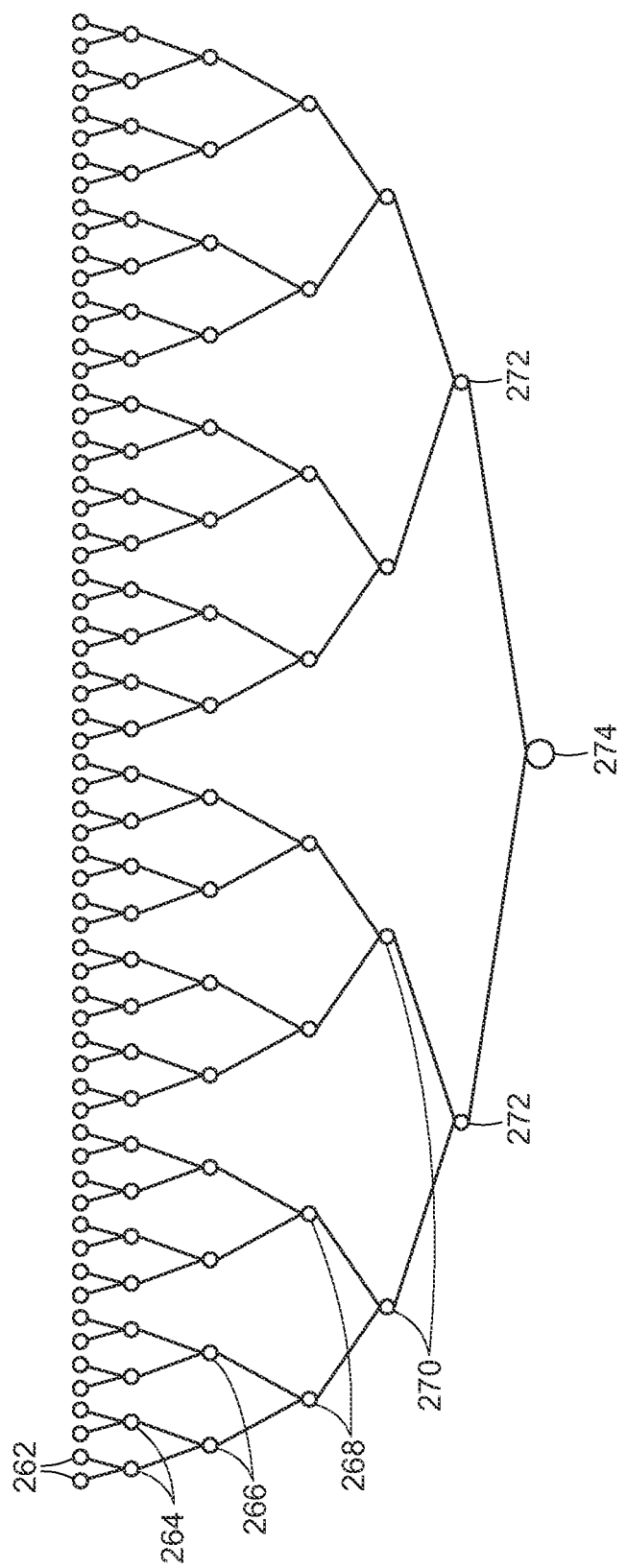
FIG. 3D illustrates a non limiting example of a hierarchical assembly strategy.

FIG. 3D is a schematic representation of an exemplary assembly strategy of hierarchical gene synthesis. Each circle represents a spot or a droplet on a solid support. As depicted in FIG. 3D, seven successive chain extension and/or ligation reactions are conducted to assemble sixty-four oligonucleotides 262 in parallel to ultimately produce a final desired assembly 274. Specifically, upon completion of synthesis of the sixty-four individual oligonucleotides 262, these are then pair-wise assembled to thirty-two subassemblies 264, which are then assembled into subassemblies 266, 268, 270, 272, until the final full-length product 274 is synthesized.

In some embodiments, methods to control temperature on-chip so that enzymatic reactions can take place on chip (PCR, ligation or any other temperature sensitive reaction) are provided. In some embodiments, a scanning laser is used to control the thermocycling on distinct spots on the solid support. The wavelength used can be chosen from wide spectrum (100 nm to 100,000 nm, i.e. from ultraviolet to infrared). In some embodiments, the feature on which the droplet is spotted comprises an optical absorber or indicator. In some other embodiment, optical absorbent material can be added on the surface of the droplet. In some embodiments, a dye can be added to the droplet reaction volume. In some embodiments, the solid support is cooled by circulation of air or fluid. The energy to be deposited can be calculated based on the absorbance behavior. In some embodiments, the temperature of the droplet can be modeled using thermodynamics. The temperature can be measured by an LCD like material or any other in-situ technology. Yet in another embodiment, the whole substrate can be heated and cooled down to allow enzymatic reactions to take place.

Figure 4:
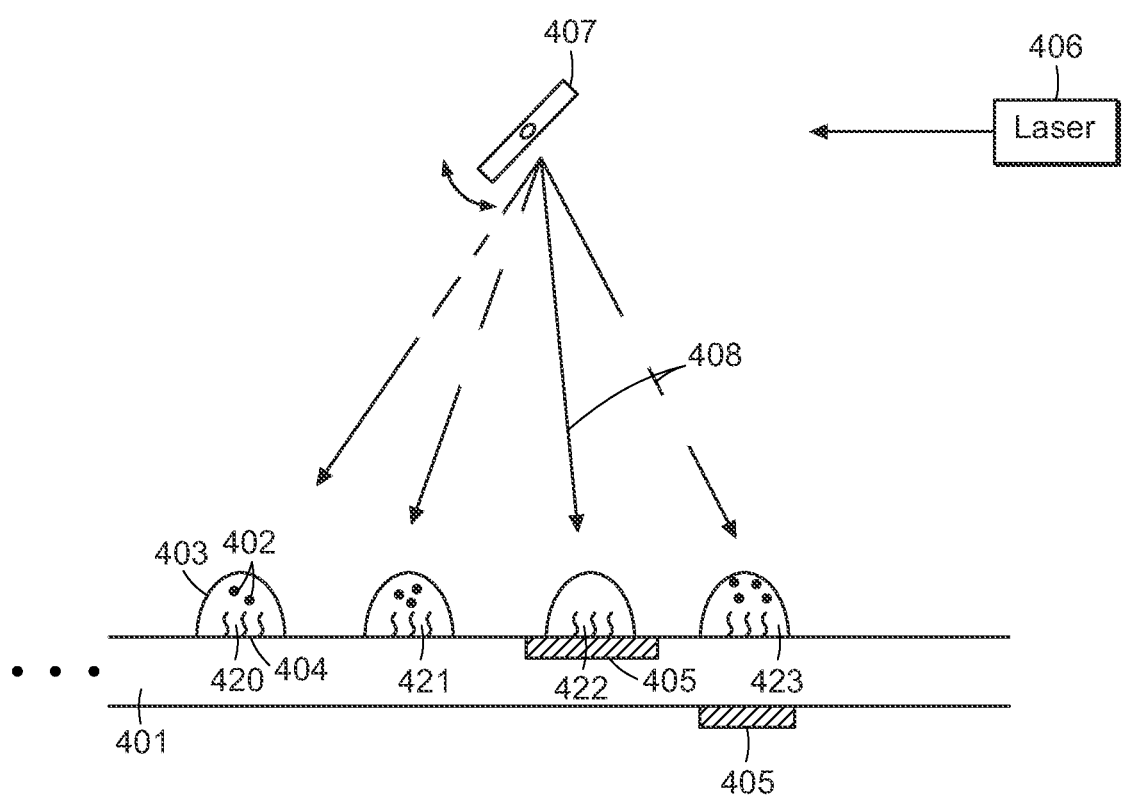
FIG. 4 illustrates an embodiment of thermal control device and procedure comprising solid support substrate (401) comprising immobilized molecules (404); an optical absorbent material (402) in the surface droplet (403), the surface droplet comprising molecules (409) in solution, an optical absorbent material (405) on the surface of 401, an optical energy source (406), a scanning setup (407), energy beams (408) and a plurality of reaction sites (420, 421, 422, 423). An optically absorbing material (405) (e.g., a dye) can be added to the surface droplet (403) (e.g., reaction volume).

One method to control the temperature of the surface droplets is by using a scanning optical energy deposition setup is shown in FIG. 4. An energy source (406) can be directed by a scanning setup (407) to deposit energy at various locations on the surface of the solid support (401) comprising attached or supported molecules (404). Optical absorbent material (402, 405) can be added on the surface of the solid support or on the surface of droplet. Optical energy source, such as a high intensity lamp, laser, or other electromagnetic energy source (including microwave) can be used. The temperature of the different reaction sites (420, 421, 422, 423, . . . ) can be controlled independently by controlling the energy deposited at each of the sites.

For example, a Digital Micromirror Device (DMD) can be used for temperature control. DMD is an microfabricated spatial optical modulator. See, for example, U.S. Pat. No. 7,498,176. In some embodiments, a DMD can be used to precisely heat selected spots or droplets on the solid support. The DMD can be a chip having on its surface, for example, several hundred thousand to several million microscopic mirrors arranged in a rectangular array which correspond to the spots or droplets to be heated. The mirrors can be individually rotated (e.g., ±10-12°), to an on or off state. In the on state, light from a light source (e.g., a bulb) is reflected onto the solid support to heat the selected spots or droplets. In the off state, the light is directed elsewhere (e.g., onto a heatsink). In one example, the DMD can consist of a 1024×768 array of 16 μm wide micromirrors. In another example, the DMD can consist of a 1920×1080 array of 10 μm wide micromirrors. Other arrangements of array sizes and micromirror widths are also possible. These mirrors can be individually addressable and can be used to create any given pattern or arrangement in heating different spots on the solid support. The spots can also be heated to different temperatures, e.g., by providing different wavelength for individual spots, and/or controlling time of irradiation.

Aspects of the methods and devices provided herein relate to determining the sequence of one or more polynucleotide and/or selectively isolating the polynucleotides having the correct sequences of interest. In some embodiments, methods to sequence verify assembled polynucleotides using high throughput sequencing are provided. In some embodiments, the assembled polynucleotides are assembled on a different station. In some embodiments, assembled polynucleotides are sequenced by synthesis. Sequence determinations can be made by any available method permitting the querying of the sequence of an individual molecule ("single molecule sequencing"), whether directly or through the querying of an amplified population of nucleic acids derived from a single molecule ("polony sequencing"). Generally, the method of sequence determination should be non-destructive, to the extent that the objective of the sequence determination is the identification of a subsequently useful oligonucleotide.

Methods of polymerase amplification and sequencing are described, for example, in U.S. Patent Application Nos. 2005-0079510 and 2006-0040297; in Mitra et al., (2003) Analytical Biochemistry 320: 55-65; Shendure et al., (2005) Science 309:1728-1732; and in Margulies et al., (2005) Nature 437:376-380, the complete disclosures of each of which are herein incorporated by reference. As discussed in Shendure et al., (2005) Science 309:1729, polony amplification can involve, for example, in situ polonies, in situ rolling circle amplification, bridge PCR, picotiter PCR, or emulsion PCR. Generally, an oligonucleotide to be amplified is prepared to include primer binding sites, whether as part of its sequence when initially synthesized or by subsequent ligation to adaptor molecules bearing the primer binding sites.

Prior to sequencing, the oligonucleotides are immobilized at distinct locations (e.g., predetermined, addressable locations or random locations) on a solid support. In the Genome Sequencer 20 System from 454 Life Sciences, for example, beads from polony amplification are deposited into wells of a fiber-optic slide. In the method of Shendure et al., beads from polony amplification are poured in a 5% acrylamide gel onto a glass coverslip manipulated to form a circular gel approximately 30 microns thick, giving a disordered monolayer.

The oligonucleotides that have been immobilized on a solid support, can then be sequenced by any non-destructive method such as sequencing by synthesis, permit the iterative interrogation of nucleobases of an oligonucleotide, which is advantageous when iterative interrogation provides a higher accuracy determination of sequence identity. For example, Margulies et al., describe a sequencing by synthesis technique in which the polony beads are sequenced in picoliter-sized wells using a pyrosequencing protocol. As another approach, Shendure et al., describe a four color sequencing by ligation method in which the identity of nucleobases is iteratively determined by ligation of anchor primers to second primers. The second primers are labeled with fluorescent dyes, the color of which identifies the nucleobase at one position in the primer; other positions are degenerate. Because ligation occurs only when the anchor primer and the second primer are properly annealed, the color of the second primer identifies the nucleobase in the oligonucleotide at the position corresponding to the non-degenerate position of the second primer. By stripping the complexes and repeating the process with different populations of second primers in which the non-degenerate position varies, nucleobases in the oligonucleotide can be iteratively identified. In yet another approach, Mitra et al., describe methods for sequencing polonies in parallel by fluorescent in situ sequential quantitation, "FISSEQ"; i.e., by performing repeated cycles of primer extension with reversibly-labeled fluorescent deoxynucleotides (for example, cycling sequentially through dATP, dCTP, dGTP, and dUTP or dTTP,). Incorporation of labeled dNTPs is monitored using a scanning fluorescence microscope and software for automated image alignment and sequence calling. If a polony has incorporated a base, it will fluoresce, thereby identifying the template base immediately 3' of the primer. Once the incorporated base is identified, the dye linker is cleaved by a reducing agent (for example, by thiol reduction), or exposure to near UV light. Cleaved dye is washed away and the cycle is repeated by adding a different dye-labeled base, washing away unincorporated dNTP, and scanning the gel. The sequence of the template nucleic acid is compiled as the primed template is interrogated at each cycle for incorporated nucleotide.

The technology provided herein can embrace any method of non-destructive sequencing. Non-limiting examples of non-destructive sequencing include pyrosequencing, as originally described by Hyman et al., (1988, Anal Biochem 74: 324-436) and bead-based sequencing, described for instance by Leamon et al., (2004, Electrophoresis 24: 3769-3777). Non-destructive sequencing also includes methods using cleavable labeled oligonucleotides, as the above described Mitra et al., (2003, Anal Biochem 320:55-62) and photocleavable linkers (Seo et al., 2005, PNAS 102: 5926-5933). Methods using reversible terminators are also embraced by the technology provided herein (Metzker et al., 1994, NAR 22: 4259-4267). Further methods for non-destructive sequencing (including single molecule sequencing) are described in U.S. Pat. Nos. 7,133,782 and 7,169,560 which are hereby incorporated by reference.

Methods to selectively extract or isolate the correct sequence from the incorrect sequences are provided herein. The term "selective isolation", as used herein, can involve physical isolation of a desired polynucleotide from others as by selective physical movement of the desires polynucleotide; selective inactivation, destruction, release, or removal of other polynucleotide than the polynucleotide of interest. It should be appreciated that a polynucleotide or library of polynucleotides assembled according to methods provided herein may include some errors that may result from sequence errors introduced during the oligonucleotides synthesis, the synthesis of the assembly nucleic acids and/or from assembly errors during the assembly reaction. Unwanted nucleic acids may be present in some embodiments. For example, between 0% and 50% (e.g., less than 45%, less than 40%, less than 35%, less than 30%, less than 25%, less than 20%, less than 15%, less than 10%, less than 5% or less than 1%) of the sequences in a library may be unwanted sequences. In one embodiment, all polynucleotide constructs are sequenced in a sequencing channel. In some embodiments, the polynucleotide constructs can be sequenced in situ on the solid support used in gene synthesis and reused/recycled therefrom. Analysis of the sequence information from the oligonucleotides permits the identification of those polynucleotides that appear to have desirable sequences and those that do not. Such analysis of the sequence information can be qualitative, e.g., providing a positive or negative answer with regard to the presence of one or more sequences of interest (e.g., in stretches of 10 to 120 nucleotides). In some embodiments, polynucleotides of interest can then be selectively isolated from the rest of the population. The sorting of individual polynucleotides can be facilitated by the use of one or more solid supports (e.g. bead, insoluble polymeric material, planar surface, etc. . . . ) to which the polynucleotides are attached. Polynucleotides determined to have the correct desired sequence can be selectively released or selectively copied.

If the polynucleotides are located in different locations e.g. in separate wells of a substrate, polynucleotides can be taken selectively from the wells identified as containing polynucleotides with desirable sequences. For example, in the apparatus of Margulies et al., polony beads are located in individual wells of a fiber-optic slide. Physical extraction of the bead from the appropriate well of the apparatus permits the subsequent amplification or purification of the desirable polynucleotides free of other contaminating polynucleotides. Alternatively, if the polynucleotides are attached to the beads using a selectively cleavable linker, cleavage of the linker (e.g., by increasing the pH in the well to cleave a base-labile linker) followed by extraction of the solvent in the well can be used to selectively isolate the polynucleotides without physical manipulation of the bead. Likewise, if the method of Shendure et al., is used, physical extraction of the beads or of the portions of the gel containing the polynucleotides of interest can be used to selectively isolate desired polynucleotides.

Certain other methods of selective isolation involve the targeting of polynucleotide molecules without a requirement for physical manipulation of a solid support. Some such methods incorporate the use of an optical system to specifically target radiation to individual polynucleotide molecules. In one embodiment, destructive radiation is selectively targeted against undesired polynucleotides (e.g., using micromirror technology) to destroy or disable them, leaving a population of oligonucleotides enriched for desired polynucleotides. This enriched population can then be released from solid support and/or amplified, e.g., by PCR.

Example of methods and systems for selectively isolating the desired product (e.g. polynucleotide of interest) are shown in FIGS. 5A-5E. In one embodiment, the system comprises a microfluidics reaction chamber (701) for sequencing reaction; individual sequencing reaction sites, containing undesirable material (702), reaction site containing desired population (703), an outlet (exit) (799) of the chamber (FIG. 5A).

In one embodiment, the correct sequence polonie is trapped using a laser tweezer or optical tweezer (FIGS. 5B-5C). Laser tweezers have been used for approximately two decades in the fields of biotechnology, medicine and molecular biology to position and manipulate micrometer-sized and submicrometer-sized particles (A. Ashkin, Science, (210), pp 1081-1088, 1980). By focusing the laser beam on the desired vessel (e.g. bead, etc.) comprising the desired polynucleotide of interest, the desired vessel remain optically trapped in the sequencing channel while the undesired polynucleotide sequences are eluted. One embodiment of the method and device is illustrated in FIG. 5B wherein the system further comprises a laser and lens system (750) to implement optical tweezers. In order to retain the vessel (s) which contains the desirable product(s), an optical tweezer setup (750) can be used. Objects at the focal point (751) of the optical tweezer can be retained while the rest of the material is washed off (towards the exit 799). Once all of the undesirable materials are washed off, the optical tweezer can be tuned off allowing the release the desired population or polynucleotide.

Another method to capture the desirable products is by ablating the undesirable products. In one embodiment, a high power laser is used to generate enough energy to disable, degrade, or destroy the product or products (e.g. polynucleotides) in areas where undesirable materials exist (763). The area where desirable products) exist (764) does not receive any destructive energy, hence preserving its contents.

In yet another implementation, the desirable product can be detected and tracked by using a camera and vision system (FIG. 5D). The vision system (775) will follow the position of the desirable product (or products), until it reaches the sorting junction (777). Desirable material will be directed towards a collection channel (774) while undesirable product (or products) directed towards another (773), where the sorting mechanism is controlled by two or more flow controllers (776).

In yet another implementation, a method to achieve "selective isolation" can involve the utilization of photopolymers to retain and trap desirable products (FIG. 5E). For example, commercial sequencing platforms, for example, those developed by PACIFIC BIOSCIENCES™, VISIGEN® Biotechnologies, Inc., and other companies utilize a surface bond polymerase in a process termed sequencing-by-synthesis. In such processes, a template (in some cases a circularized template) is captured by the surface attached polymerase during sequencing. The template remains captured after sequencing is complete, and this allows for a "selective isolation" method to be applied to this class of next generation sequencing platforms. In one embodiment, after sequencing is complete (FIG. 5E(1)), and the amplicons are removed via washing (FIG. 5E(2)), a photosensitive polymer precursor can be introduced to the surface that encapsulates the areas of interest (FIG. 5E(3)). The sold support can be, for example, a glass substrate and a polymerase can be immobilized on the solid support. The wells can be wells in a layer, for example, a metal layer on the solid support. In FIG. 5E(1), a template strand can be associated with the polymerase, and the amplicons can be synthesized from the template using the polymerase and labeled nucleotides in solution. A pattern of radiation (controlled by scanning laser, a DMD, or other optical manipulation) is introduced to allow polymerization of the photo-sensitive polymer to take place on the locations where product capture is desirable. The unexposed photo-sensitive polymer precursors are removed in a wash, leaving the undesirable products exposed to the fluid environment, allowing exposure to buffers, enzymes, and chemical to facilitate the removal of these products (FIG. 5E(4)). Subsequently, the polymerized polymers can be removed, exposing the desired products (FIG. 5E(5)). These products can be eluted from the surface for collection, or amplified in situ with the surface-attached polymerase to produce an enriched volume of the final product (FIG. 5E(6)).

In some embodiments, assembled library nucleic acids may be amplified, sequenced or cloned. In some embodiments, a host cell may be transformed with the assembled library nucleic acids. Library nucleic acids may be integrated into the genome of the host cell. In some embodiments, the library nucleic acids may be expressed, for example, under the control of a promoter (e.g., an inducible promoter). Individual variant clones may be isolated from a library. Nucleic acids and/or polypeptides of interest may be isolated or purified. A cell preparation transformed with a nucleic acid library, or an isolated nucleic acid of interest, may be stored, shipped, and/or propagated (e.g., grown in culture).

Aspects of the methods and devices provided herein may include automating one or more acts described herein. In some embodiments, one or more steps of an assembly reaction may be automated using one or more automated sample handling devices (e.g., one or more automated liquid or fluid handling devices). Automated devices and procedures may be used to deliver reaction reagents, including one or more of the following: starting nucleic acids, buffers, enzymes (e.g., one or more ligases, polymerases, nucleases, helicases, and/or other enzymes), nucleotides, salts, and any other suitable agents such as stabilizing agents. Automated devices and procedures also may be used to control the reaction conditions. For example, an automated thermal cycler may be used to control reaction temperatures and any temperature cycles that may be used. In some embodiments, a scanning laser may be automated to provide one or more reaction temperatures or temperature cycles suitable for incubating polynucleotides. Similarly, subsequent analysis of assembled polynucleotide products may be automated. For example, sequencing may be automated using a sequencing device and automated sequencing protocols. Additional steps (e.g., amplification, cloning, etc.) also may be automated using one or more appropriate devices and related protocols. It should be appreciated that one or more of the device or device components described herein may be combined in a system (e.g., a robotic system) or in a micro-environment (e.g., a micro-fluidic reaction chamber).

Assembly reaction mixtures (e.g., liquid reaction samples) may be transferred from one component of the system to another using automated devices and procedures (e.g., robotic manipulation and/or transfer of samples and/or sample containers, including automated pipetting devices, micro-systems, etc.). The system and any components thereof may be controlled by a control system.

In some embodiments, a droplet can be dried (e.g., via evaporation of the solvent) and/or heated to an elevated temperature to achieve enzyme deactivation after a desired/predetermined enzymatic reaction step. Such enzyme deactivation provides methods for enzyme control in addition to the other methods disclosed herein (e.g., washing, chemical, buffer conditions, temperature control of the droplet, and the like).

After dry deactivation, the surface location (e.g., where the evaporated droplet was located) can be rehydrated (e.g., to re suspend the molecules that had become temporarily surface-supported). In this way, the functionality of molecules that are not affected by the dry down and heat treatment can be preserved while the functionality of molecules that are affected by the dry down and/or heating can be selectively deactivated and/or destroyed.

Accordingly, method steps and/or aspects of the devices provided herein may be automated using, for example, a computer system (e.g., a computer controlled system). A computer system on which aspects of the technology provided herein can be implemented may include a computer for any type of processing (e.g., sequence analysis and/or automated device control as described herein). However, it should be appreciated that certain processing steps may be provided by one or more of the automated devices that are part of the assembly system. In some embodiments, a computer system may include two or more computers. For example, one computer may be coupled, via a network, to a second computer. One computer may perform sequence analysis. The second computer may control one or more of the automated synthesis and assembly devices in the system. In other aspects, additional computers may be included in the network to control one or more of the analysis or processing acts. Each computer may include a memory and processor. The computers can take any form, as the aspects of the technology provided herein are not limited to being implemented on any particular computer platform. Similarly, the network can take any form, including a private network or a public network (e.g., the Internet). Display devices can be associated with one or more of the devices and computers. Alternatively, or in addition, a display device may be located at a remote site and connected for displaying the output of an analysis in accordance with the technology provided herein. Connections between the different components of the system may be via wire, optical fiber, wireless transmission, satellite transmission, any other suitable transmission, or any combination of two or more of the above.

Each of the different aspects, embodiments, or acts of the technology provided herein can be independently automated and implemented in any of numerous ways. For example, each aspect, embodiment, or act can be independently implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

In this respect, it should be appreciated that one implementation of the embodiments of the technology provided herein comprises at least one computer-readable medium (e.g., a computer memory, a floppy disk, a compact disk, a tape, etc.) encoded with a computer program (i.e., a plurality of instructions), which, when executed on a processor, performs one or more of the above-discussed functions of the technology provided herein. The computer-readable medium can be transportable such that the program stored thereon can be loaded onto any computer system resource to implement one or more functions of the technology provided herein. In addition, it should be appreciated that the reference to a computer program which, when executed, performs the above-discussed functions, is not limited to an application program running on a host computer. Rather, the term computer program is used herein in a generic sense to reference any type of computer code (e.g., software or microcode) that can be employed to program a processor to implement the above-discussed aspects of the technology provided herein.

It should be appreciated that in accordance with several embodiments of the technology provided herein wherein processes are stored in a computer readable medium, the computer implemented processes may, during the course of their execution, receive input manually (e.g., from a user).

Accordingly, overall system-level control of the assembly devices or components described herein may be performed by a system controller which may provide control signals to the associated nucleic acid synthesizers, liquid handling devices, thermal cyclers, sequencing devices, associated robotic components, as well as other suitable systems for performing the desired input/output or other control functions. Thus, the system controller along with any device controllers together form a controller that controls the operation of a nucleic acid assembly system. The controller may include a general purpose data processing system, which can be a general purpose computer, or network of general purpose computers, and other associated devices, including communications devices, modems, and/or other circuitry or components to perform the desired input/output or other functions. The controller can also be implemented, at least in part, as a single special purpose integrated circuit (e.g., ASIC) or an array of ASICs, each having a main or central processor section for overall, system-level control, and separate sections dedicated to performing various different specific computations, functions and other processes under the control of the central processor section. The controller can also be implemented using a plurality of separate dedicated programmable integrated or other electronic circuits or devices, e.g., hard wired electronic or logic circuits such as discrete element circuits or programmable logic devices. The controller can also include any other components or devices, such as user input/output devices (monitors, displays, printers, a keyboard, a user pointing device, touch screen, or other user interface, etc.), data storage devices, drive motors, linkages, valve controllers, robotic devices, vacuum and other pumps, pressure sensors, detectors, power supplies, pulse sources, communication devices or other electronic circuitry or components, and so on. The controller also may control operation of other portions of a system, such as automated client order processing, quality control, packaging, shipping, billing, etc., to perform other suitable functions known in the art but not described in detail herein.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

EXAMPLES

Example 1: Utilize Solid-Attached Molecular Library

A solid support with a high density of high diversity DNA molecules attached is used as the destination surface. The DNA molecules on the surface are arranged in a pattern that corresponds to a known map stored in a computer. On the surface, several alignment features are placed next to the DNA molecule pattern, preferably one at each of the four corners of the DNA pattern. The placement of the alignment feature is known in relation to the DNA pattern.

First, as illustrated in FIG. 1A and FIG. 1B, a set of droplets (106, and 170) is deposited next to the alignment features. The positional difference between these droplets and the alignment features is measured with a microscope objective and camera. The positional difference is compared to the desired positions of the droplets, and the offset of the alignments is calculated. This set of calculated values are stored and used to compensate for the alignment between the source plate and the destination surface.

In the source plate, the reagent wells (105) contain reagents to amplify, digest, and assemble DNA molecules. For example, first, a DNA polymerase, appropriate primers, salts, and dNTPs are dispensed to a site on the surface of the solid support containing a template sequence attached to the said surface. After the dispensing, the temperature of the surface is modulated to induce polymerase chain reaction (PCR). The result is that the template sequences are amplified into solution in the droplet.

After amplification, a polymerase disabling agent (for example epoxy ATP) is added to the reaction volume. A few cycles of PCR reaction takes place, and disables the polymerase enzymes.

The primer sites on the amplification product in solution are removed by using a restriction enzyme that cuts outside of its recognition frame. The restriction enzyme is added to the reaction site, and allowed to digest the substrate to produce only the construction pieces. The restriction enzymes are heat in-activated.

At this point, the double stranded material in each of the droplet contains, among other molecules, hybridized oligonucleotides suitable for subsequent assembly. In a massively parallel reaction, all of the reaction sites on the solid support surface can be treated in parallel. For example, in a case where there are 8 fragments are assembled together in a 3 step process, A, B, C, D, E, F, G, H are all processed simultaneously in 8 individual reaction volumes.

In the next step, as illustrated in FIG. 3A, two reaction volumes are combined, i.e., A and B, C and D, E and F, G and H, forming 4 step one reactions. During the combining of these droplets, DNA ligase is added to the reaction volumes, and the samples are treated to allow ligation reaction to complete. Once this step (step one) is complete, these four larger droplets are further aggregated into two even larger droplets, for example, A+B is combined with C+D, and E+F is combined with G+H. More reagent is added during the combination process, and allowed to ligate under suitable conditions. Finally, the two large droplets are combined into a final droplet, with the addition of reagents for subsequent reactions, such as DNA ligase. The final volume is allowed to react at the optimal condition.

Example 2: Utilize Molecular Library without Surface-Bond Amplification

A solid support with a high density of high diversity DNA molecules attached is used as the destination surface. The DNA molecules on the surface are arranged in a pattern that corresponds to a known map stored in a computer. On the surface, several alignment features are placed next to the DNA molecule pattern, preferably one at each of the four corners of the DNA pattern. The placement of the alignment feature is known in relation to the DNA pattern.

First, as illustrated in FIGS. 1A and 1B, a set of droplets (106, and 170) is deposited next to the alignment features. The positional difference between these droplets and the alignment features is measured with a microscope objective and camera. The positional difference is compared to the desired positions of the droplets, and the offset of the alignments is calculated. This set of calculated values are stored and used to compensate for the alignment between the source plate and the destination surface.

Instead of adding reagents that will amplify the surface attached DNA molecules, a reagent is added which can cleave the DNA molecules from the surface. After cleaving, these DNA molecules can participate in subsequent reactions in a similar manner as outlined in the previous example.

Example 3: Cleaving without Using Liquid Reagents

In another example, the strategy outlined in Example 2 can be simplified to not use liquid cleaving reagents. Surface attached (covalent) DNA molecules can be translated into surface supported DNA molecules through a process of gaseous cleavage using amine gas. In this process, the solid support with surface attached molecules is exposed to a amine gas under elevated pressure and/or temperature, this process is shown to be useful to cleave the covalent bond that attaches the DNA molecules to the solid support. Subsequent steps after this gaseous cleavage is identical to those of example 1 and 2.

The resulting surface-supported high density molecular array library can be accessed (e.g., to the resolution of individual spots), for example, by the various droplet-based technologies disclosed herein. In particular, the application of gaseous cleavage to high-density molecular libraries can offer a useful and unique advantage. During the gaseous cleavage of a high-density library, the elements of the molecular library can be transformed from being surface-attached to surface-supported. Therefore, the information of the location of each of the elements is preserved, allowing for subsequent manipulation and/or access to the surface-supported molecules. In conjunction with the techniques disclosed herein, the application of gaseous cleavage can allows for each and every element on a high-density molecular library to be individually accessed.

Cleaved oligos can be use directly to participate in the assembly reaction, or can be amplified via PCR prior to the assembly reactions.

Example 4: Using a Scanning Laser for Thermal Cycling

After dispensing PCR reagents onto the solid support (as in Example 1), a scanning laser is used for thermocycling. The temperature of the individual sites can be modulated to perform PCR reaction with different thermal parameters (temperature profile) at each of the sites. For example, depending on sequence information, site A may need a different optimal temperature profile compared to site B, and it is possible to accommodate such temperature differences. Also, mixed reaction can take place on the same solid support, i.e., site C requires a PCR reaction while at the same time, site D requires a ligation or digestion reaction. In such a case, the temperature profile at site C can be one for a PCR reaction while the temperature at site D can be maintained at a steady temperature for ligation or digestion.

Example 5: Commercial Microarray-Based Assembly

The solid support can be a DNA microarray (e.g., a chip). The microarray can be constructed, custom ordered or purchased from a commercial vendor (e.g., Agilent, Affymetrix, Nimblegen). Commercially available DNA microarrays generally have an arrayed series of microscopic spots of DNA oligonucleotides, each containing picomoles of a specific DNA sequence (e.g., 20 to 120 nucleotides). The spots combined can represent a genomic or subgenomic feature (e.g., a human chromosome, the *Drosophila* genome, the yeast genome, etc.). Thus commercial DNA microarrays can be used as source of oligonucleotides for gene and/or genome assembly. Some of the advantages include: commercial microarrays have high density and diversity of source materials, and can be washed and reused multiple times; cost per base of raw material can be reduced by a factor of 10 to 100, 100 to 1,000, or 1,000 to 10,000 compared to other methods (e.g., de novo synthesis); and high diversity allows for higher synthesis output by parallel processing. Thus repeatable, reliable, automated DNA assembly can be achieved using commercial microarrays.

An example of commercial microarray is the Agilent DNA microarrays. These microarrays can have 1×1M, 1×244K, 2×105K, 4×44K, or 8×15K spots one a single slide, and about $10^5$ to about $10^{15}$ molecules per spot. The spot size and spacing between neighboring spots can each be less than about 100 microns. In various examples, the spot size can be less than about 100, 95, 90, 85, 80, 75, 70, 65, 60, 55, 50, 45, 40, 35, 30, 25, 20, 15, or 10 microns. In various examples, the spacing between spots can be less than about 100, 95, 90, 85, 80, 75, 70, 65, 60, 55, 50, 45, 40, 35, 30, 25, 20, 15, or 10 microns. Spot sizes and spacing can vary independently and can be uniform or non-uniform across a microarray. A database of 28 million+ predesigned, in silico-validated aCGH probes that span exonic, intronic, and intergenic DNA regions can be deposited on these microarrays.

1. On-Chip Oligonucleotide Synthesis

Oligonucleotides can be synthesized on a microarray using the attached oligonucleotides as template. For example, oligonucleotide synthesis can be achieved within a droplet covering each spot by solid phase PCR. The droplet can contain enzymes, buffers, dNTPs, primers, etc. In some cases, the PCR primers are attached to a solid surface (Adessi et al., Nucleic Acids Research, 2000, Vol. 28, No. 20 e87). Another technique hinges on the attachment of the template to a surface (Bennett S., Pharmacogenomics, 2004 June; 5(4):433-8).

DNA microarrays can have very high density of oligonucleotides on the surface, which can generate steric hindrance to polymerases needed for PCR. Theoretically, the oligonucleotides are generally spaced apart by about 2 nm to about 6 nm. For polymerases, a typical 6-subunit enzyme can have a diameter of about 12 nm. Therefore the microarray needs to be custom treated to address the surface density issue such that the spacing of surface-attached oligonucleotides can accommodate the physical dimension of the enzyme. For example, a subset of the oligonucleotides can be chemically or enzymatically cleaved, or physically removed from the microarray. Other methods can also be used to modify the oligoucleotides such that when primers are applied and annealed to the oligonucleotides, at least some 3' hydroxyl groups of the primers (start of DNA synthesis) are accessible by polymerase. The number of accessible 3' hydroxyl groups per spot can be stochastic or fixed. For example, the primers, once annealed, can be treated to remove some active 3' hydroxyl groups, leaving a stochastic number of 3' hydroxyl groups that can be subject to chain extension reactions. In another example, a large linker molecule (e.g., a concatamer) can be used such that one and only one start of synthesis is available per spot, or in a subset of the oligonucleotides per spot.

Figure 6:
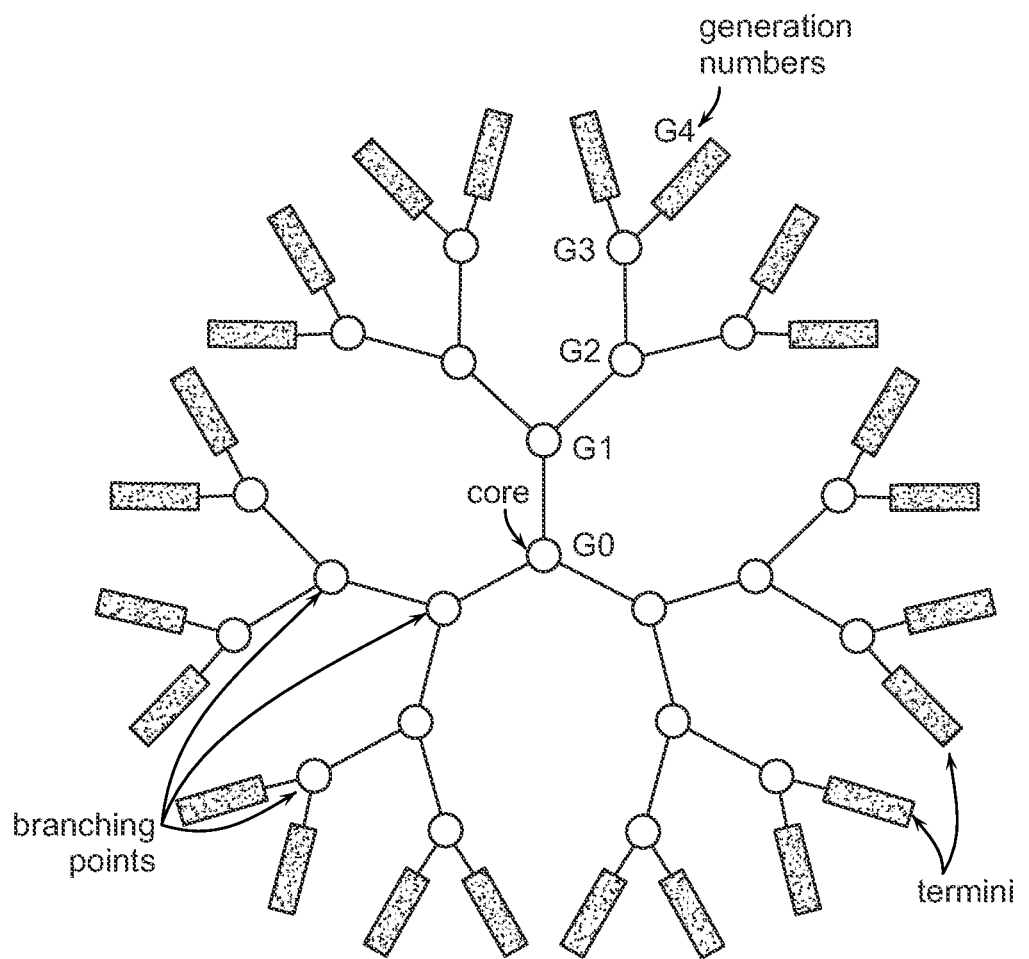
FIG. 6 illustrates an exemplary structure of a dentron molecule.

In some embodiments, a dendron can be used for modification of microarray surface. A dendron is a molecular structure that resembles a tree. See FIG. 6. By branching out away from the surface of the microarray, a dendron can reduce the steric hindrance effects. The dendron can also be produced in a way that some or all of the branches are chemically inert, with exception to one or more reactive groups (e.g., for the attachment of one or more oligonucleotides, resulting in one or more 3' end as the start of DNA synthesis per dendron). Doing so can reduce the surface density of reactive groups, leading to a less dense DNA microarray.

In some embodiments, the modification of the surface-attached molecular density can be modulated by chemical cleaving after completing the synthesis of the molecular library. A cleaving site can be designed into the synthesis process to allow the harvesting of the synthesized products. For example, amine can be used for cleaving oligonucleotides from the surface. Such post-synthesis cleaving step can be applied to reduce the surface molecular density. In one implementation, the cleaving process can be allowed to proceed only for a short period of time or under other non-optimal reaction conditions to achieve in-complete cleavage of the synthesized product. The remaining (e.g., uncleaved) product that remains attached to the surface will have a reduced surface molecular density, which can facilitate subsequent enzymatic or chemical processing.

Figure 7A:
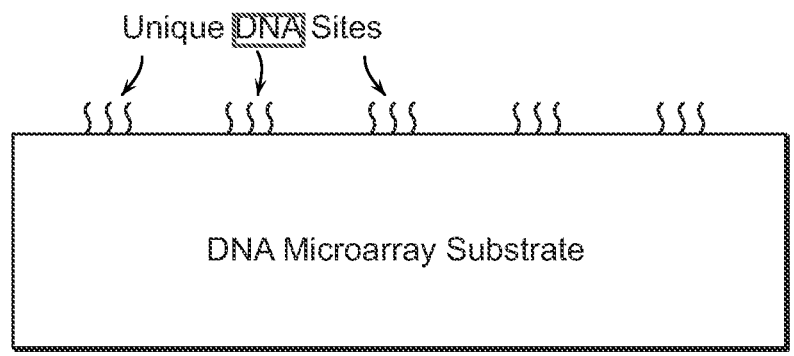
FIG. 7A illustrates a DNA library on a microarray.
Figure 7B:
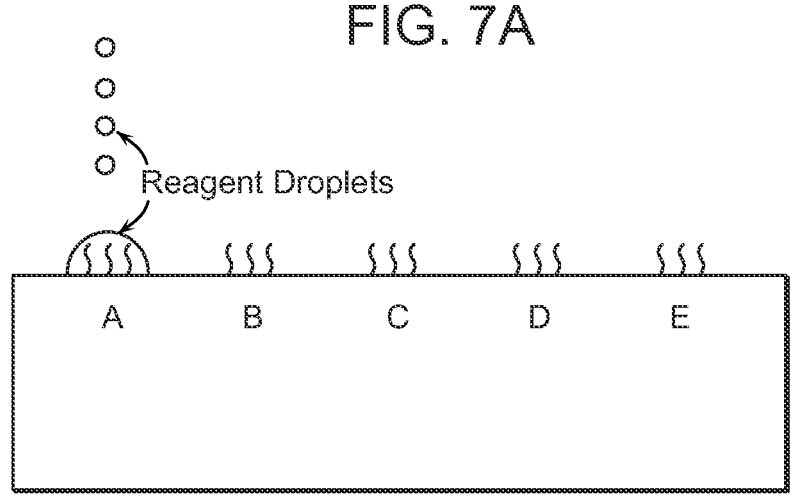
FIG. 7B illustrates that picoliter and sub picoliter volume droplets can be used to access the large library of material on a DNA microarray.

Microarray features are in general too small for conventional fluid handling technologies. Pico-liter and sub pico-liter volume droplets can be used to access the large library of material available on a DNA microarray. See FIGS. 7A-7B. This access is possible because the dimension of the droplets matches that of the features on the microarray. Pico-liter and sub pico-liter droplet based liquid handling and manipulation can be achieved using e.g., the inkjet technology. To perform chemistry at the scale of the microarray, if assuming a surface liquid-solid contact angle of 90 degrees, the volumes for each spot is between about 0.3 pL to about 2 nL. These volumes coincides with inkjet droplet technology well. For example, a typical inkjet printer is capable of producing 1.5 to 10 pL droplets, while other commercial ultrasonic dispensing techniques can produce droplets down to 0.6 pL.

Figure 8:
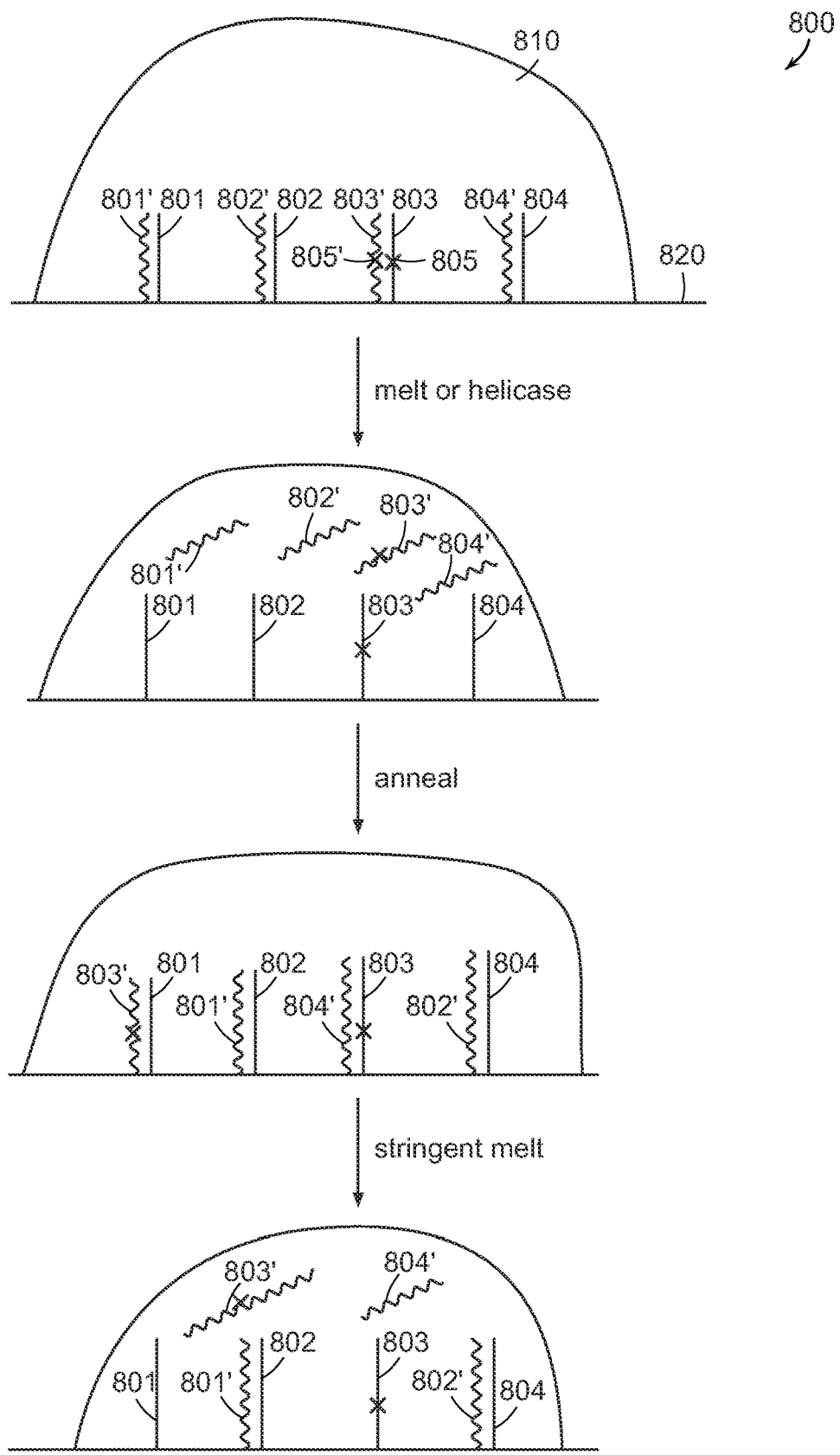
FIG. 8 illustrates an exemplary method of error filtration.

A droplet 810, as illustrated in FIG. 8, can be dispensed (e.g., ink jetted) on a microarray 800. The droplet 810 can contain various reagents such as enzymes, buffers, dNTPs, primers, etc. The droplet 810 covers a spot 820 (a feature corresponding to a predefined sequence) on the microarray 800. For purpose of illustration only, four oligonucleotides, 801, 802, 803, 804 are shown, while many more oligonucleotides having the same sequence are also present on spot 820 but not shown. PCR can be carried out to synthesize oligonucleotides 801', 802', 803', 804' complementary to template oligonucleotides 801, 802, 803, 804 that are attached to spot 820.

Any DNA polymerase having a chain extension activity can be suitable for the on-chip oligonucleotide synthesis. In one embodiment, strand displacing polymerase exo-(having no exonuclease activity) can be used for isothermal nucleic acid amplification. The polymerase can be used to extend once or more than once (e.g., multiple times) per template oligonucleotide. For example, the polymerase can bind a template and extend, fall off the end of the template, and bind to the same or another surface template and extend again. This leads to a linear (not exponential) amplification. The resulted linearly amplified pool of products are single-stranded DNA (ssDNA).

Primers can be included in the reaction mixture for linear and/or exponential amplification. The primers can have the same sequence or different sequences. In one embodiment, a pair of primers, one sense strand and the other anti-sense strand, can be added to the reaction mixture such that amplification is exponential and yields double-stranded DNA (dsDNA). The primer sequences attached to the PCR products (e.g., ssDNA or dsDNA) can be cleaved by using a Uracil DNA glycosylase. The cleaved products can be digested into single, double, triple, or other short nucleotide sequences by using a) the same Uracil DNA glycosylase; and/or b) a primer design that has the following pattern: UXUXU . . . XUXU (where X is any base) or UXnUXn UXn . . . XnU (where Xn is a series of X numbered n, e.g., ATG can be represented by X3). In the case of Xn, n can be 0, 1, 2, 3, 4, 5, 6, 7, 8, 9, 10, 11, 12, or more. In another example, the primer sequence is in the pattern of UnXnUnXn . . . XnUnXn, where Un is n repeats of U (e.g., U3 is UUU).

After the PCR reaction, the polymerase can be deactivated to prevent interference with subsequent steps. A heating step (e.g., high temperatures) can denature and deactivate most enzymes but not likely to affect thermally stable PCR DNA polymerase. A non-thermal stable version of polymerase can be used in PCR, which are generally less optimized in error rate and speed. Alternatively, adenosine riboepoxide triphosphate nucleotide (epoxy dATP) can be used to inactivate polymerase. Epoxy dATP can be incorporated into a lengthening DNA polymer and form a covalent bond to the enzyme during incorporation, hence block the active site of the enzyme. Another method is to remove or wash away all reagents, including the polymerase, leaving only the duplexes formed between the template oligonucleotides and synthesized oligonucleotides on the microarray surface. For example, liquids can evaporate in a vacuum while heating. Enzymes can be heat deactivated at the same time, with or without liquid. Heat deactivation of enzymes in the absence of liquid can be advantageous without hurting (e.g., hydrolysis) other biologically active molecules (e.g., DNA molecules). After deactivation, a washing step can be used to remove deactivated enzymes and other non-surface bound molecules. Next, the microarray surface (e.g., location of drop foot print) can be re-activated by adding a solvent (e.g., water) to the surface.

In some embodiments, spots on the microarray can contain oligonucleotides that are substantially complementary (e.g., 50%, 60%, 70%, 80%, 90%, 95%, 98%, 99%, or 100%). As a result, the PCR products synthesized from such two spots are also substantially complementary and can form duplexes when combined (e.g., by merging two droplets). These duplexes can be subjected to error and/or mismatch recognition and removal (see below; e.g., using a mismatch recognition protein such as MutS), where mismatch-free duplexes can be exponentially amplified through additional rounds of PCR.

2. Error Control

With reference to FIG. 8, template oligonucleotides 801, 802, 803, 804 can have inherent errors as they are generally chemically synthesized (e.g., deletions at a rate of 1 in 100 bases and mismatches and insertions at about 1 in 400 bases). Assuming an average error rate of 1 in 300 bases and an average template oligonucleotide size of 70 bases, every 1 in 4 template oligonucleotides will contain an error compared to a reference sequence (e.g., the wide-type sequence of a gene of interest). For example, template oligonucleotide 803 can contain an error 805 which can be a mismatch, deletion, or insertion. In PCR synthesis, the error 805 is retained in the synthesized oligonucleotide 803' as error 805'. Additional errors (not shown) can be introduced during PCR. Methods for error correction and/or filtration are needed for high-fidelity gene synthesis/assembly.

In one embodiment, error-containing oligonucleotides are removed by a method illustrated in FIG. 8. PCR products (duplexes 801-801', 802-802', 803-803', 804-804') are denatured by melting the duplexes (e.g., at elevated temperature, using a helicase, etc.), forming free oligonucleotides 801', 802', 803', 804'. In some embodiments, using a helicase to melt duplexes can provide for isothermal denaturing without elevating the temperature.

Next, under annealing conditions (e.g., lower temperature), oligonucleotides 801', 802', 803', 804' will randomly anneal to template oligonucleotides 801, 802, 803, 804. By way of example, new duplexes 801-803', 802-801', 803-804' and 804-802' can be formed. 802-801' and 804-802' are error-free duplexes, whereas 801-803' and 803-804' each contain a mismatch between the two complementary strands. All duplexes within a spot are then subject to a stringent melting step to denature 801-803' and 803-804', leaving 802-801' and 804-802' intact. Oligonucleotides 803'

(containing error 805') and 804' can then be removed or washed away. Error-free oligonucleotides 801' and 802' can be melted and recovered in a droplet for subsequent amplification, ligation, and/or chain extension. These steps can be repeated multiple times to enrich for error-free oligonucleotides, as microarray 800 can be washed and reused at least several times.

The conditions for stringent melt (e.g., a precise melting temperature) can be determined by observing a real-time melt curve. In an exemplary melt curve analysis, PCR products are slowly heated in the presence of double-stranded DNA (dsDNA) specific fluorescent dyes (e.g., SYBR Green, LCGreen, SYTO9 or EvaGreen). With increasing temperature the dsDNA denatures (melts), releasing the fluorescent dye with a resultant decrease in the fluorescent signal. The temperature at which dsDNA melts is determined by factors such as nucleotide sequence, length and GC/AT ratio. Melt curve analysis can detect a single base difference. Various methods for accurate temperature control at individual spots can be used as disclosed above.

Another embodiment of the invention is directed toward the recognition and removal of double-stranded oligonucleotides containing sequence mismatch errors. It is particularly related to the removal of error-containing oligonucleotides generated, for example, by chemical or biological synthesis by removing mismatched duplexes using mismatch recognition proteins (MMBP). For methods and materials known in the art related to error detection and correction using mismatch binding proteins, see e.g., International Publication No. WO 03/054232, and U.S. Patent Publication Nos. 20050227235 and 20060127926; incorporated by reference in their entirety. For example, MutS error filtration can be used to remove error-containing oligonucleotides, in which a bulge-binding protein is used to remove mismatch-containing DNA double-strands. In some embodiments, all double-strands can be chemically or enzymetically cleaved off the microarry. The protein-DNA complex can be captured by an affinity of the MMBP protein to, e.g., a specific antibody, immobilized nickel ions (e.g., where MMBP is produced as a his-tag fusion), streptavidin (e.g., where MMBP has been modified by the covalent addition of biotin) or by any other such mechanisms as are common to the art of protein purification. These affinity-based capture methods can be assisted by acoustic, magnetic, and/or optical separation methods. Alternatively, the protein-DNA complex is separated from the pool of error-free DNA sequences by a difference in mobility, such as by size-exclusion column chromatography or by electrophoresis.

Error filtration using MMBP proteins can also be achieved without cleaving the PCR products off the microarray. For example, the presence of the protein-DNA complex can change helicase activity in melting double-strands; under suitable conditions (e.g., low temperature, short reaction time) only mismatch-free double-strands that are not bound by MMBP proteins are melted thereby releasing error-free synthesized oligonucleotides. In some embodiments, the MMBP protein (e.g., MutS) can be irreversibly complexed with a mismatch recognition protein by the action of a chemical crosslinking agent (e.g., dimethyl suberimidate, DMS), or of another protein (such as MutL). This blocks access to error-containing oligonucleotides attached on the microarry in subsequent steps (e.g., additional rounds of PCR). The population of double strands that are error free can then be subjected to one or more of: denaturing, chain extension, annealing, restriction, and ligation.

3. Hierarchical Assembly

Step-wise hierarchical assembly (e.g., as discussed above) can be used to construct polynucleotides. Neighboring droplets, each containing a unique sequence, can be manipulated (e.g., moved, merged) to aggregate and assemble the content of individual droplets in a way that minimizes the complexity in biochemistry, hence improving assembly efficiency. A droplet can be moved from one oligonucleotide-containing spot to another oligonucleotide-containing spot, to allow assembly (e.g., ligation based, chain extension based) of the two different oligonucleotides. Two neighboring droplets can be merged by dispensing liquid (e.g., a solution containing for example, buffer, dNTPs, and enzymes that allow ligation and/or chain extension) in between. Two neighboring droplets can also be moved to an oligonucleotide-free position where pair-wise assembly can be performed without any oligonucleotide annealing back to the oligonucleotides attached on the microarray.

Mechanical wave actuated delivery techniques (e.g., a surface acoustic wave device, a piezoelectric inkjet device) can be used to move or hop droplets. More advanced droplet manipulations, such as moving and splitting droplets can be facilitated by using electrostatic or magnetic force (Cho et. al., Journal of Microelectromechanical Systems, 12(1), 2003, pp. 70-80).

To facilitate automation, the single-step polymerase assembly multi-plexing (PAM) reaction developed by Tian et al. (*Nature* 432, 1050-1054 (23 Dec. 2004)) can be used for multiple gene syntheses from a combined/merged pool of oligonucleotides. For PAM, gene-flanking primer pairs can be added to the pool of oligonucleotides (with the primer pairs at a higher concentration than the oligonucleotides), together with thermostable polymerase and dNTPs. Extension of overlapping oligonucleotides and subsequent amplification of multiple full-length genes can thus be accomplished in a one-step reaction. Different generic adaptor sequences can be incorporated into the ends of each gene or gene set, and a set of complementary adaptor-primer pairs can be pre-synthesized to avoid the cost of synthesizing gene-specific PAM primer pairs and to facilitate automation.

4. Sequence Verification

After assembly, all products can be pooled and all impurities (e.g., enzymes, dNTPs, primers) can be removed. The assembled products can be a complex pool of fragments containing correct and incorrect assemblies. This pool of fragments can be sequenced and the desired products having the correct sequences can be recovered. A preparative sequencing step can be performed to find and recover the correct sequences from among the mixed population of DNA molecules. A $2_{nd}$ or $3_{rd}$ generation DNA sequencer (e.g. a polonator) or, for example, a system such as a PACIFIC BIOSCIENCE™ SMRT™ system can be used, e.g., for single molecule sequencing, as discussed above.

In some embodiments, qualitative sequencing can also meet the goal of verifying the correct sequence without employing a sequencer. A microarray having substantially the same features as the microarray previously used in oligonucleotide synthesis and assembly can provide such qualitative sequencing information. For example, the same microarray previously used in oligonucleotide synthesis and assembly can be washed, dried, and reused, thereby reducing costs. Alternatively, a new microarray having substantially the same features can be used; after sequencing, this microarray can be washed, dried, and reused for synthesis, assembly, and/or sequencing.

In qualitative sequencing, the assembled products can hybridize to oligonucleotides immobilized on the microarray under hybridization conditions (e.g., proper temperature, buffer), where a positive hybridization signal within a particular feature indicates the presence of the sequence corresponding to that particular feature. For example, the hybridization buffer can contain double-stranded DNA (dsDNA) specific fluorescent dyes (e.g., SYBR Green, LCGreen, SYTO9 or EvaGreen); thus presence or absence of fluorescence at different features represents positive or negative hybridization, respectively. These individual features on the microarray can thus be used as sequencing patches that can provide qualitative information with regard to the sequence of the assembled products.

In various embodiments, the sequencing step can be massively parallel to match the output from the assembly process. For example, multiple microfluidics chips can be operated simultaneously to achieve high throughput. In one embodiment, 2, 4 or even 8 microfluidics chips (cores) can be operated in the same sequencing machine at the same time, to allow up to 8 genes to be assembled during a single run. Where a microarray is used, as many genes can be assembled at once as the amount of DNA material is available on a single chip. Multiple microarrays can also be used at the same time to further increase parallelism.

Example 6: Synthesis of Oligonucleotides Having a Predefined Sequence

A plurality of oligonucleotides having a predefined sequence are synthesized by providing a plurality of support-bound template oligonucleotides in a solution comprising a primer, a polymerase and nucleotides, wherein each of the plurality of template oligonucleotides comprises a predefined sequence and includes a primer binding site, and wherein the primer comprises at least one nuclease recognition site. The plurality of template oligonucleotides are exposed to conditions suitable for primer hybridization and polymerase extension, thereby extending the primers to produce a complementary oligonucleotide for each of the plurality of template oligonucleotides. The hybridized complementary oligonuceotides are released from the template oligonucleotides into solution and exposed to a nuclease under conditions suitable for the nuclease to bind to the nuclease recognition site on the primer and cleave the primer from complementary oligonucleotide. The complementary and template oligonucleotides are exposed to conditions suitable for hybridization; thereby to produce a plurality of partially double-stranded oligonucleotides. The plurality of partially double-stranded oligonucleotides are washed and then the complementary oligonucleotides are melted from the template oligonucleotides.

According to another version, a microarray of single stranded DNA template molecules is provided. Second, a primer, dNTP, and a polymerase is dispensed (e.g., ink jetted) onto the microarray in spots. The primer includes at least one, and preferably more than one, nuclease site. Next, a product is produced by priming the template and extending an oligonucleotide on the template. Then, the product is melted apart from the template. The product includes the primer sequence as well as the payload sequence. Subsequently, a nuclease is dispensed (e.g., ink jetted) into the spots. If the primer includes only one nuclease site, it is preferably located between the primer sequence and the payload sequence, so that the nuclease cleaves the primer from the payload. When the primer includes more than one nuclease site, they are preferably located between the primer sequence and the payload sequence as well as being dispersed within the primer, so that the nuclease cleaves the primer from the payload in addition to cleaving the primer into smaller oligonucleotides. After cleavage, the payload is rehybridized onto the single stranded DNA template. Due to differences in length and thus melting temperature, the payload can hybridize at a temperature where the cleaved primer remains in solution. After rehybridization, the unbound primer and/or primer fragments are removed by washing. After the primer and/or primer fragments (and, in some examples other unwanted elements, for example, nuclease) are removed, the payload can be melted apart from the template and is available is in a substantially pure solution.

EQUIVALENTS

The present invention provides among other things novel methods and apparatuses for high-fidelity gene assembly. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

INCORPORATION BY REFERENCE

Reference is made to PCT Publication Nos. WO07136736 and WO08024319, and U.S. Pat. No. 6,248,521. All publications, patents and sequence database entries mentioned herein are hereby incorporated by reference in their entirety as if each individual publication or patent was specifically and individually indicated to be incorporated by reference.

The invention claimed is:

1. A method for removing error-containing oligonucleotides synthesized on a solid support, the method comprising:
   (a) synthesizing a first plurality of oligonucleotides in a chain extension reaction, wherein a second plurality of oligonucleotides immobilized on the solid support serves as a template in the chain extension reaction, and wherein the second plurality of oligonucleotides comprises one or more oligonucleotides comprising a sequence error;
   (b) denaturing products of the chain extension reaction;
   (c) contacting the first plurality of oligonucleotides with the second plurality of oligonucleotides under hybridization conditions to form duplexes; and
   (d) separating error-containing oligonucleotides from oligonucleotides with error-free sequences.

2. The method of claim 1, wherein the error-containing oligonucleotides are separated from oligonucleotides with error-free sequences using a component which actively selects for a sequence error.

3. The method of claim 2, wherein the sequence error selecting component comprises a mismatch recognition protein MutS or a functional variant of MutS.

4. The method of claim 1, wherein the chain extension reaction forms homo-duplexes.

5. The method of claim 1, wherein the duplexes formed in step (c) comprise homo-duplexes and hetero-duplexes.

6. The method of claim 5, wherein each hetero-duplex comprises at least one sequence error.

7. The method of claim 6, wherein the sequence error is a sequence mismatch.

8. The method of claim 6, wherein the step of separating comprises:
(a) denaturing the hetero-duplexes under stringent melt conditions without denaturing the homo-duplexes;
(b) removing the denatured error-containing oligonucleotides from the solid support; and
(c) denaturing the homo-duplexes, thereby forming a purified plurality of oligonucleotides with error-free sequences.

9. A method for removing error-containing oligonucleotides synthesized on a solid support, the method comprising:
(a) synthesizing a first plurality of oligonucleotides in a chain extension reaction on a first spot on said solid support, wherein a second plurality of oligonucleotides immobilized on said first spot on said solid support serve as templates in the chain extension reaction;
(b) denaturing products of the chain extension reaction;
(c) contacting the first plurality of oligonucleotides with a third plurality of oligonucleotides under hybridization conditions to form duplexes, wherein said third plurality of oligonucleotides are synthesized on a second spot on said solid support substantially in parallel to step a), and wherein said first and third plurality of oligonucleotides comprise sequences that are complementary; and
(d) separating error-containing oligonucleotides from oligonucleotides with error-free sequences.

10. The method of claim 9, wherein the error-containing oligonucleotides are separated from oligonucleotides with error-free sequences using a component that actively selects for a sequence error.

11. The method of claim 10, wherein the sequence error selecting component comprises a mismatch recognition protein MutS or a functional variant of MutS.

12. The method of claim 9, wherein the chain extension reaction forms homo-duplexes.

13. The method of claim 9, wherein the duplexes formed in step (c) comprise homo-duplexes and hetero-duplexes.

14. The method of claim 13, wherein each hetero-duplex comprises at least one sequence error.

15. The method of claim 14, wherein the sequence error is a sequence mismatch.

16. The method of claim 14, wherein the step of separating comprises:
(a) denaturing the hetero-duplexes under stringent melt conditions without denaturing the homo-duplexes;
(b) removing the denatured error-containing oligonucleotides from the solid support; and
(c) denaturing the homo-duplexes, thereby forming a purified plurality of oligonucleotides with error-free sequences.

* * * * *